United States Patent
Lombardo et al.

[11] Patent Number: 6,166,050
[45] Date of Patent: Dec. 26, 2000

[54] 3,4-DIAMINO-3-CYCLOBUTENE-1,2-DIONE DERIVATIVES WHICH INHIBIT LEUKOCYTE ADHESION MEDIATED BY VLA-4

[75] Inventors: Louis J. Lombardo, Belle Mead; Joan Sabalski, Hamilton, both of N.J.

[73] Assignee: American Home Products Corporation, Madison, N.J.

[21] Appl. No.: 09/458,852

[22] Filed: Dec. 10, 1999

Related U.S. Application Data

[60] Provisional application No. 60/155,221, Dec. 14, 1998.

[51] Int. Cl.$^7$ .......................... C07D 213/02; A61K 31/44
[52] U.S. Cl. ................. 514/352.18; 514/567; 514/357; 514/252.12; 514/399; 514/419; 514/332; 546/335; 546/255; 562/457; 544/360; 544/399; 548/340.1; 548/494
[58] Field of Search ..................... 546/335, 255; 562/457; 514/357, 567, 252.12, 252.18, 332, 399, 419; 544/360, 399; 548/340.1, 494

[56] References Cited

U.S. PATENT DOCUMENTS 5,168,103  12/1992  Kinney et al. .................... 514/221

FOREIGN PATENT DOCUMENTS 05229999  9/1993  Japan .
WO9427947  12/1994  WIPO .
WO9850347  11/1998  WIPO .

OTHER PUBLICATIONS van Dinther–Janssen et al., Annals. Rheumatic Dis. 52: 672 (1993).
Elices et al., J. Clin, Invest. 93: 405 (1994).
Postigo et al., J. Clin. Invest. 89: 1445 (1991).
Paul et al., Transpl. Proceed., 25: 813 (1993).
Okahara et al., Can. Res. 54: 3233 (1994).
Paavonen et al., Int. J. Can. 58: 298 (1994).
Schadendorf et al., J. Path., 170: 429 (1993).
Elices et al., Cell, 60: 577–584 (1990).
Osborn, Cell, 62: 3–6 (1990).
Springer, Nature, 346: 425–434 (1990).
Vedder et al., Surgery, 106: 509 (1989).
Pretolani et al., J. Exp. Med., 180: 795 (1994).
Abraham et al., Clin. Invest. 93: 776 (1994).
Mulligan et al., Immunology, 150: 2407 (1993).
Cybulsky et al., Science, 251: 788 (1991).
Li et al., Atheroscler. Thromb., 13: 197 (1993).
Sasseville et al., Am. J. Path., 144: 27 (1994).
Yang et al., Proc. Nat. Acad. Science (USA) 90: 10494 (1993).
Burkly et al., Diabetes, 43: 529 (1994).
Baron et al., J. Clin. Invest. 93: 1700 (1994).
Hamann et al., J. Immunology, 152: 3282 (1994).
Yednock et al., Nature, 356; 63 (1992).
Baron et al., J. Exp. Med. 177: 57 (1993).

*Primary Examiner*—Zinna Northington Davis
*Attorney, Agent, or Firm*—Rebbeca R. Barrett

[57] ABSTRACT

Compounds of the formula

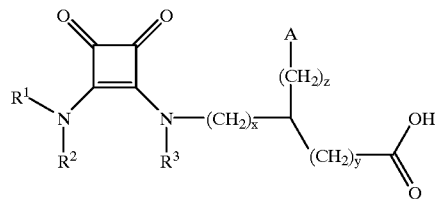

which inhibit leukocyte adhesion mediated by interaction of the $\alpha_4\beta_1$ integrin (VLA-4) with its counterreceptor VCAM-1, and their use for the treatment of inflammatory and autoimmune diseases.

39 Claims, No Drawings

3,4-DIAMINO-3-CYCLOBUTENE-1,2-DIONE DERIVATIVES WHICH INHIBIT LEUKOCYTE ADHESION MEDIATED BY VLA-4

This application claims the benefit U.S. Provisional Application No. 60/155,221 filed Dec. 14, 1998.

FIELD OF THE INVENTION

This invention relates to novel N-substituted 3,4-diamino-3-cyclobutene-1,2-dione derivatives which inhibit leukocyte adhesion mediated by interaction of the $\alpha_4\beta_1$ integrin (VLA-4) with its counterreceptor VCAM-1, and their use for the treatment of inflammatory and autoimmune diseases.

BACKGROUND OF THE INVENTION

VLA-4 (also referred to as $\alpha_4\beta_1$ integrin and CD49d/CD29), first identified by Hemler and Takada (Hemler and Takada, European Patent Application, Publication No. 330,506, published Aug. 30, 1989) is a member of the $\beta_1$ integrin family of cell surface receptors, each of which comprises two subunits, an $\alpha_4$ chain and a $\beta_1$ chain. There are at least nine $\beta_1$ integrins, all sharing the same $\beta_1$ chain and each having a distinct $\alpha$ chain. These nine receptors all bind a different complement of the various cell matrix molecules such as fibronectin, laminin and collagen. VLA-4, for example, binds to fibronectin. VLA-4 is unique among $\beta_1$ integrins in that it also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for fibronectin and VCAM-1 binding activities and each activity has been shown to be inhibited independently (Elices, et al., *Cell*, 60:577–584 (1990)).

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer (Springer, *Nature*, 346:425–434 (1990)) and Osborn (Osborn, *Cell*, 62:3–6 (1990)).

Inflammatory brain disorders, such as multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to injured tissue causing still further insult (Vedder, et al., *Surgery*, 106:509 (1989)). Other inflammatory conditions mediated by an adhesion mechanism include asthma (Pretolani, et al., *J. Exp. Med.*, 180:795 (1994); Abraham, et al., *Clin. Invest.*, 93:776 (1994); Mulligan, et al., *Immunology*, 150:2407 (1993)), Alzheimer's disease, atherosclerosis (Cybulsky, et al., *Science*, 251:788 (1991); Li, et al., *Atheroscler. Thromb.*, 13:197 (1993)), AIDS dementia (Sasseville, et al., *Am. J. Path.*, 144:27 (1994)), diabetes (Yang, et al., *Proc. Nat. Acad. Science (USA)*, 90:10494 (1993); Burkly, et al., *Diabetes*, 43:526 (1994); Baron, et al., *J. Clin. Invest.*, 93:1700 (1994)), inflammatory bowel disease (Hamann, et al., *Immunology*, 152:3238 (1994)), multiple sclerosis (Yednock, et al., *Nature*, 356:63 (1992); Baron, et al., *J. Exp. Med.*, 177:57 (1993)), rheumatoid arthritis (van Dinther-Janssen, et al., *Annals. Rheumatic Dis.*, 52:672 (1993); Elices, et al., *J. Clin. Invest.*, 93:405 (1994); Postigo, et al., *J. Clin. Invest.*, 89:1445 (1991)), tissue transplantation (Paul, et al., *Transpl. Proceed.*, 25:813 (1993), and tumor metastasis (Okahara, et al., *Can. Res.*, 54:3233 (1994); Paavonen, et al., *Int. J. Can.*, 58:298 (1994); Schadendorf, et al., *J. Path.*, 170:429 (1993)).

Because of the significance of VLA-4 in inflammatory and autoimmune conditions, it is desirable to test for the presence of VLA-4 in biological samples and for compounds which inhibit cell adhesion.

Individually, each receptor/ligand interaction is rapidly reversible; however, during the process of cell adhesion, multiple $\alpha_4\beta_1$ integrin receptors on one cell engage multiple VCAM-1 ligands on another cell, and together provide a strong and stable adhesive bond. In order to prevent cell adhesion, small molecule inhibitors of $\alpha_4\beta_1$ integrin must achieve a high degree of receptor occupancy for disruption of a significant number of these adhesive interactions. Furthermore, due to the multivalency of the adhesive interaction, inhibitory compounds exhibit a very steep titration curve, since inhibition begins with 85–90% receptor occupancy and is complete when 95–100% of the receptors are occupied. With such a narrow dynamic range there is considerable assay to assay variation in cell-based adhesion studies. An assay which can detect the presence of a single VCAM-1 molecule with a single receptor and thus prevent assay to assay variation is desired.

N-substituted 3,4-diamino-3-cyclobutene-1,2-dione derivatives have been taught. Japanese Patent JP05229999 A2 930907 discloses cyclobutenediones which are symmetrically disubstituted with α-amino acids.

U.S. Pat. No. 5,168,103 issued Dec. 1, 1992, and assigned to American Home Products, describes cyclobutenedione derivatives having formula (2)

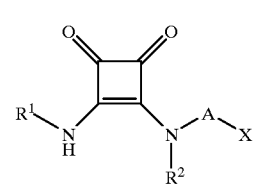

where A is alkylene or alkenylene. These compounds are taught to be useful as N-methyl-D-aspartate antagonists.

DESCRIPTION OF INVENTION

This invention provides novel compounds of Formula I

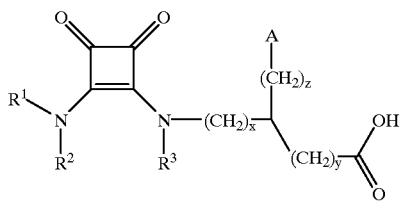

wherein
$R^1$ is alkyl, aryl, heteroaryl, aralkyl or heteroaralkyl;
$R^2$ is H, alkyl, aryl, heteroaryl, aralkyl, or heteroaralkyl; or
$R^1$ and $R^2$ may be taken together to form a saturated or unsaturated heterocycloalkyl;
$R^3$ is H, alkyl, aryl, heteroaryl, aralkyl, or heteroaralkyl;
A is aryl or heteroaryl; and
x, y and z are independently 0, 1, 2, 3, or a pharmaceutical salt thereof.

In some preferred embodiments of the present invention R1 is alkyl of 1 to 10 carbon atoms, aralkyl of 7 to 11 carbon atoms, or heteroaralkyl of 7 to 11 members having 1 to 3 heteroatoms. In still more preferred embodiments of the present invention $R^1$ is straight chain alkyl of 4 to 8 carbon atoms, benzyl, benzhydryl, phenethyl, pyridylmethyl or pyridylethyl.

$R^2$ is preferably hydrogen, alkyl of 1 to 10 carbon atoms or aralkyl of 7 to 11 carbon atoms. More preferably $R^2$ is hydrogen, alkyl of 1 to 6 carbon atoms, benzyl or naphthylmethyl.

Alternatively, when $R^1$ and $R^2$ are taken together, they preferably form a substituted heterocycloalkyl of 5 to 7 members having 1 to 3 heteroatoms selected from N, O and S.

A is preferably substituted or unsubstituted aryl. When A is substituted the substituent is preferably selected from —$NR^4COR^5$, —$OCONR^6R^7$ or —$O(CH_2)mNR^6R^7$ wherein $R^4$ is hydrogen or alkyl of 1 to 3 carbon atoms, $R^5$ is substituted or unsubstituted aryl, heteroaryl or heterocycloalkyl, $R^6$ and $R^7$ are independently, hydrogen or alkyl of 1 to 3 carbon atoms, or $R^6$ and $R^7$, taken together may form a substituted heterocycloalkyl, and m is an integer from 1 to 6.

In some embodiments of the present invention it is preferred that x and y are 0 and z is 1. $R^3$ is preferably hydrogen in some aspects of the invention.

For purposes of defining preferred substituted heterocycloalkyl, preferred substituents are alkyl of 1 to 3 carbon atoms, aryl, —$COR^8$ or —$COOR^9$ wherein $R^8$ is alkyl of 1 to 3 carbon atoms, aryl of 5 or 6 carbon atoms or aralkyl of 6 or 7 carbon atoms, and $R^9$ is hydrogen, alkyl of 1 to 3 carbon atoms, aryl of 5 or 6 carbon atoms or aralkyl of 6 or 7 carbon atoms.

In some embodiments of the present invention $R^1$ is alkyl, aralkyl or heteroaralkyl, A is phenyl, x and y are 0, and z is 1.

More preferred compounds of the present invention are the following compounds:

[2-(Benzylamino)-3,4-dioxo-cyclobut-1-enyl]-L-phenylalanine;
[2-(benzhydrylamino)-3,4-dioxo-cyclobut-1-enyl]-L-phenylalanine;
2-{2-[2-(1H-Indol-3-yl)-ethylamino]-3,4-dioxo-cyclobut-1-enylamino}-L-phenylalanine;
{3,4-Dioxo-2-[(pyridin-3-ylmethyl)-amino]-cyclobut-1-enyl}-L-phenylalanine;
[2-(Benzyl-hexyl-amino)-3,4-dioxo-cyclobut-1-enyl]-L-phenylalanine;
(2-Dibenzylamino-3,4-dioxo-cyclobut-1-enylamino)-L-phenylalanine;
(S)-2-(2-Dihexylamino-3,4-dioxo-cyclobut-1-enylamino)-3-phenyl-propionic acid;
(S)-2-[2-(Hexyl-naphthalen-2-ylmethyl-amino)-3,4-dioxo-cyclobut-1-enylamino]-3-phenyl-propionic acid;
(S)-2-{2-[(4-Dimethylamino-benzyl)-hexyl-amino]-3,4-dioxo-cyclobut-1-enylamino}-3-phenyl-propionic acid;
N-[3,4-Dioxo-2-(4-phenyl-piperazin-1-yl)-cyclobut-1-en-1-yl]-L-phenylalanine;
(S)-2-[2-(4-Acetyl-piperazin-1-yl)-3,4-dioxo-cyclobut-1-enylamino]-3-phenyl-propionic acid;
(S)-3-(4-Benzoylamino-phenyl)-2-(2-dihexylamino-3,4-dioxo-cyclobut-1-enylamino)-propionic acid;
(S)-3-(1-Benzyl-1H-imidazol-4-yl)-2-(2-dihexylamino-3,4-dioxo-cyclobut-1-enylamino)-propionic acid;
N-(2-Dihexylamino-3,4-dioxo-cyclobut-1-enylamino)-O-(3-dimethylamino-propyl)-L-tyrosine;
N-[2-[Methyl[2-(4-pyridinyl)ethyl]amino]-3,4-dioxo-1-cyclobuten-1-yl]-4-[(4-pyridinylcarbonyl)amino]-L-phenylalanine;
N-[2-[Methyl(2-phenylethyl)amino]-3,4-dioxo-1-cyclobuten-1-yl]-4-[(4-pyridinylcarbonyl)amino]-L-phenylalanine;
N-[2-(Dihexylamino)-3,4-dioxo-1-cyclobuten-1-yl]-4-[(4-pyridinylcarbonyl)amino]-L-phenylalanine;
N-[2-(Methyl-pyridin-3-ylmethyl-amino)-3,4-dioxo-cyclobut-1-enyl]-4-[(pyridine-4-carbonyl)-amino]-L-phenylalanine;
N-[2-(Dihexylamino)-3,4-dioxo-1-cyclobuten-1-yl]-4-[(3-pyridinylcarbonyl)amino]-L-phenylalanine;
N-[2-[Methyl[2-(4-pyridinyl)ethyl]amino]-3,4-dioxo-1-cyclobuten-1-yl]-4-[(3-pyridinylcarbonyl)amino]-L-phenylalanine;
N-[2-(Methyl-pyridin-3-ylmethyl-amino)-3,4-dioxo-cyclobut-1-enyl]-4-[(pyridine-3-carbonyl)-amino]-L-phenylalanine;
N-{2-[Methyl-(2-pyridin-4-yl-ethyl)-amino]-3,4-dioxo-cyclobut-1-enyl}-L-phenylalanine;
N-[2-(Dihexylamino)-3,4-dioxo-1-cyclobuten-1-yl]-{4-[4-(N-carboxybenzoyl)piperidinylcarbonyl]amino}-L-phenylalanine methyl ester;
(2S)-3-(4-Dimethylcarbamoyloxy-phenyl)-2-[2-(methyl-phenethyl-amino)-3,4-dioxo-cyclobut-1-enylamino]-propionic acid;
(2S)-2-(2-Dihexylamino-3,4-dioxo-cyclobut-1-enylamino)-3-(4-dimethylcarbamoyloxy-phenyl)-propionic acid;
(2S)-3-(4-Dimethylcarbamoyloxy-phenyl)-2-[2-(methyl-pyridin-3-ylmethyl-amino)-3,4-dioxo-cyclobut-1-enylamino]-propionic acid;
(2S)-3-(4-Dimethylcarbamoyloxy-phenyl)-2-{2-[methyl-(2-pyridin-4-yl-ethyl)-amino]-3,4-dioxo-cyclobut-1-enylamino}-propionic acid;
(2S)-3-[4-(4-methylpiperazinyl)carbamoyloxy-phenyl]-2-[2-(methyl-phenethyl-amino)-3,4-dioxo-cyclobut-1-enylamino]-propionic acid;
(2S)-3-[4-(4-methylpiperazinyl)carbamoyloxy-phenyl)-2-{2-[methyl-(2-pyridin-4-yl-ethyl)-amino]-3,4-dioxo-cyclobut-1-enylamino}-propionic acid; and
(2S)-3-[4-(4-methylpiperazinyl)carbamoyloxy-phenyl)-2-{2-dihexylamino]-3,4-dioxo-cyclobut-1-enylamino}-propionic acid; or a pharmaceutical salt thereof.

"Alkyl" as used herein means a branched or straight chain having from 1 to 10 carbon atoms and more preferably from 1 to 8 carbon atoms. Exemplary alkyl groups include methyl, ethyl, propyl, isopropyl, butyl, isobutyl, t-butyl, pentyl and hexyl. Alkyl may be substituted and unsubstituted.

"Aryl" as used herein means mono or bicyclic aromatic ring having from 5 to 12 carbon atoms. Monocyclic rings preferably have 5 or 6 members and bicyclic rings preferably have 8, 9 or 10 membered ring structures. Exemplary aryl groups include phenyl and naphthyl. Aryl may be substituted or unsubstituted.

"Aralkyl" as used herein means an aryl-alkyl group in which the aryl and alkyl group are previously defined. Exemplary aralkyl groups include benzyl and phenethyl. The aralkyl may be substituted or unsubstituted.

"Halogen" is chlorine, fluorine, iodine or bromine.

"Heteroaryl" whether used alone or as part of a group such as "heteroaralkyl" means 5 to 10 membered mono or bicyclic aromatic ring having from 1 to 3 heteroatoms selected from N, O and S. Exemplary heteroaryls include pyridyl, pyrazinyl, pyridazinyl, pyrimidinyl, indolyl, imidazolyl, pyrazolyl and pyrrolyl. Preferred heteroaryl groups include 1H-indoly-3-yl, pyridin-3-yl, pyridin-4-yl, and 1H-imidazol-4-yl. The heteroaryl may be substituted or unsubstituted.

"Heteraralkyl" means an heteroaryl-alkyl group in which the heteroaryl and alkyl are as previously described. Exemplary heteroaralkyls include pyridylmethyl, pyridylethyl, thienylethyl, thienylmethyl, indolylmethyl, and furylmethyl. The heteraralkyl may be substituted or unsubstituted.

Heterocycloalkyl refers to a monocycloalkyl having from 5 to 10 members including one or more heteroatoms selected from N, O or S. The heterocycloalkyl may be saturated or unsatured and may be substituted or unsubstituted.

Suitable substituents, unless otherwise noted are unsubstituted and include, but are not limited to, alkyl of 1 to 3 carbon atoms, halogen, —CN, —NO$_2$, perhaloalkyl of 1 to 3 carbon atoms, aryl, aralkyl, —NR$^4$COR$^5$, —CO$_2$R$^4$, —OR$^4$, —OCONR$^6$R$^7$ or —O(CH$_2$)mNR$^6$R$^7$ wherein R$^4$ is hydrogen, alkyl of 1 to 3 carbon atoms, or aralkyl of 7–10 carbon atoms, R$^5$ is aryl, heteroaryl or heterocycloalkyl, R$^6$ and R$^7$ are independently, hydrogen or alkyl of 1 to 3 carbon atoms, or R$^6$ and R$^7$, taken together may form a heterocycloalkyl, and m is an integer from 1 to 6.

Carbon number refers to the number of carbons in the carbon backbone and does not include carbon atoms occurring in substituents thereof.

Where terms are used in combination, the definition for each individual part of the combination applies unless defined otherwise.

Pharmaceutically acceptable salts are the acid addition salts which can be formed from a compound of the above general formula and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid, and the like.

The compounds of this invention contain a chiral center, providing for various seteroisomeric forms of the compounds such as racemic mixtures as well as the individual optical isomers. The individual isomers can be prepared directly or by asymmetric or stereospecific synthesis or by conventional separation of optical isomers from the racemic mixture.

Novel compounds of Formula I are prepared by the sequential addition of appropriate amine nucleophiles to 3,4-diethoxy-3-cyclobutene-1,2-dione in alcoholic solvent, followed by hydrolysis of the precursor carboxylic acid ester to the parent acid by treatment with aqueous base as shown in the following reaction schemes.

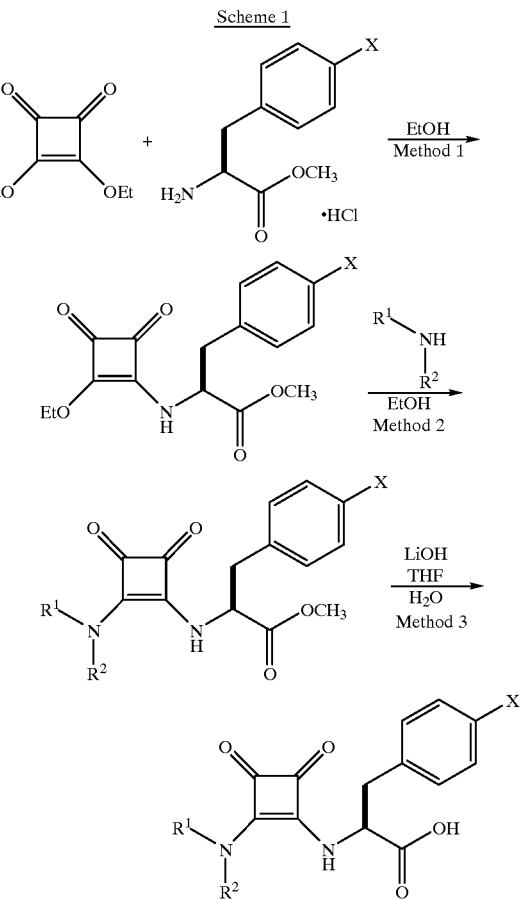

Scheme 1

In the case where the product of Method 1 contains X=OH, the corresponding carbamates are prepared as in Scheme 2.

Scheme 2

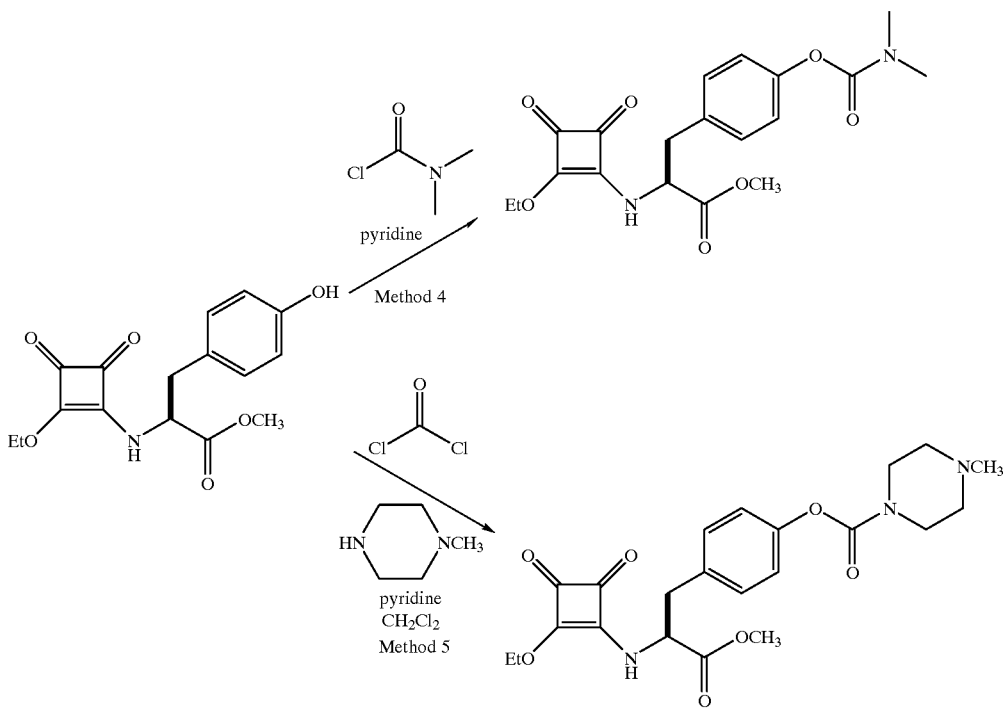

The carbamate products are then further elaborated via Method 2 above.

The method of preparing compounds of Formula I as described above are exemplified in the following specific examples. These examples are illustrative and are not meant to be limiting to this disclosure in any way. Other methods of preparing compounds of the present invention may be apparent to those skilled in the art. Reactants and reagents used are either commercially available or can be prepared according to standard literature procedures.

EXAMPLE 1

(Method 1)

[2-Ethoxy-3,4-dioxo-cyclobut-1-enyl]-L-phenylalanine methyl ester

To a stirred solution of L-phenylalanine methyl ester HCl (2.0 mmol, 431 mg) in absolute ethanol (20 mL) was added triethylamine (2.2 mmol, 202 mg; 278 μL) and the resulting solution was stirred at room temperature for 15 minutes. Subsequently, neat 3,4-diethoxy-3-cyclobutene-1,2-dione (2 mmol, 340 mg; 296 μL) was added dropwise and the resulting solution was stirred at room temperature overnight, during which a white solid precipitated out of solution. The volatiles were removed in vacuo and the residue was taken up in EtOAc and partitioned between EtOAc and water. The organics were dried ($Na_2SO_4$) and purified by flash chromatography ($SiO_2$:1) 20% EtOAc/hexane; 2) 30% EtOAc/hexane; 3) 40% EtOAc/hexane) to afford the title compound as a colorless oil (551 mg; 85%).

$^1$H NMR (DMSO-$d_6$, 300 MHz) δ9.1 (br d, 1H), 7.24 (m, 6H), 4.88 (m, 1H), 4.55 (m, 3H), 4.16 (m, 2H), 3.23 (dd, 1H), 2.96 (m, 1H), 1.30 (m, 2H).

EXAMPLE 2

(Method 2)

[2-(Benzylamino)-3,4-dioxo-cyclobut-1-enyl]-L-phenylalanine methyl ester

To a stirred solution of [2-ethoxy-3,4-dioxo-cyclobut-1-enyl]-L-phenylalanine methyl ester (0.33 mmol, 100 mg) in absolute ethanol (3 mL) was added neat benzylamine (0.36 mmol, 39 mg; 40 μL) dropwise at room temperature. The resulting solution was stirred at room temperature overnight, during which a white solid precipitated out of solution. The volatiles were removed in vacuo and the residue was taken up in EtOAc and partitioned between EtOAc and water. The organics were dried ($Na_2SO_4$), concentrated in vacuo and purified by flash chromatography ($SiO_2$:EtOAc/hexane) to afford the title compound as a white solid (113 mg; 94%).

$^1$H NMR (DMSO-$d_6$, 400 MHz) δ7.85 (br s, 1H), 7.66 (br s, 1H), 7.37 (m, 2H), 7.26 (m, 6H), 7.13 (m, 2H), 5.1 (m, 1H), 4.68 (m, 2H), 3.68 (s, 3H), 3.16 (dd, 1H, J=13.9, 5.4 Hz), 3.03 (m, 1H).

EXAMPLE 3
(Method 3)

[2-(Benzylamino)-3,4-dioxo-cyclobut-1-enyl]-L-phenylalanine

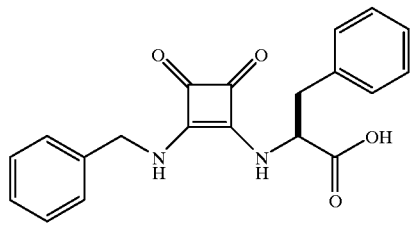

To a stirred solution of [2-(benzylamino)-3,4-dioxo-cyclobut-1-enyl]-L-phenylalanine methyl ester (0.16 mmol, 60 mg) in THF (5 mL) was added aqueous LiOH (1.0 M; 0.16 mmol; 160 µL) and the resulting solution was stirred at room temperature for 3 hours. The volatiles were removed in vacuo and the residue partitoned between 0.1M acetic acid and EtOAc. The organics were dried ($Na_2SO_4$) and concentrated in vacuo to afford the title compound as a white solid, mp=215–216° C. (33 mg; 59%).

$^1$H NMR (DMSO-$d_6$, 400 MHz) δ13.1 (br s, 1H), 7.89 (br s, 1H), 7.59 (br s, 1H), 7.37 (m, 2H), 7.26 (m, 6H), 7.14 (m, 2H), 4.91 (m, 1H), 4.68 (m, 2H), 3.17 (m, 1H), 3.01 (m, 1H).

MS(EI, m/e (%)) 350 (17, M$^+$), 259 (16), 91 (100).

EXAMPLE 4
(Method 2)

[2-(benzhydrylamino)-3,4-dioxo-cyclobut-1-enyl]-L-phenylalanine methyl ester

Following the procedure of Method 2 above, the title compound was obtained from [2-ethoxy-3,4-dioxo-cyclobut-1-enyl]-L-phenylalanine methyl ester and diphenylmethylamine in 88% yield.

$^1$H NMR (DMSO-$d_6$, 400 MHz) δ8.38 (br s, 1H), 7.68 (br s, 1H), 7.39 (m, 4H), 7.26 (m, 9H), 7.12 (m, 2H), 6.33 (m, 1H), 5.01 (m, 1H), 3.69 (s, 3H), 3.16 (dd, 1H, J=13.4; 5.6 Hz), 3.05 (dd, 1H, J=13.4; 5.6 Hz).

EXAMPLE 5
(Method 3)

[2-(benzhydrylamino)-3,4-dioxo-cyclobut-1-enyl]-L-phenylalanine

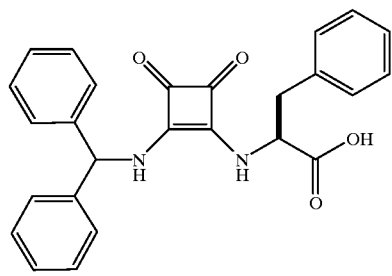

Following the procedure of Method 3 above, the title compound was obtained in 76% yield as a white solid, mp=187–188° C.

$^1$H NMR (DMSO-$d_6$, 400 MHz) δ13.2 (br s, 1H), 8.41 (br s, 1H), 7.62 (be s, 1H), 7.38 (m, 4H), 7.30 (m, 2H), 7.24 (m, 7H), 7.13 (d, 2H, J=7.02 Hz), 6.34 (m, 1H), 4.90 (M, 1H), 3.16 (dd, 1H, J=13.7; 4.9 Hz), 3.05 (m, 1H).

MS ((+)FAB, m/e (%)) 449 (14, (M+Na)$^+$), 427 (45, (M+H)$^+$), 217 (33), 167 (100).

IR (KBr, cm$^{-1}$) 3200, 1790, 1730, 1640, 1575, 1530, 1440, 710.

Anal. Calc'd for $C_{26}H_{22}N_2O_4$.0.25 $H_2O$: C, 72.45; H, 5.26; N, 6.50.

Found: C, 72.69; H, 5.22; N, 6.67.

EXAMPLE 6
(Method 2)

2-{2-[2-(1H-Indol-3-yl)-ethylamino]-3,4-dioxo-cyclobut-1-enylamino}-L-phenylalanine methyl ester Following the procedure of Method 2 above, the title compound was obtained from [2-ethoxy-3,4-dioxo-cyclobut-1-enyl]-L-phenylalanine methyl ester and tryptamine in 86% yield.

$^1$H NMR (DMSO-$d_6$, 400 MHz) δ10.88 (s, 1H), 7.68 (br s, 1H), 7.57 (d, 2H, J=7.8 Hz), 7.33 (d, 1H, J=7.8 Hz), 7.23 (m, 3H), 7.12 (m, 3H), 7.07, (dt, 1H, J=7.03; 1.1 Hz), 6.96 (dt, 1H, J=7.03; 1.1 Hz), 5.0 (m, 1H), 3.79 (m, 2H), 3.67 (s, 3H), 3.13 (M, 1H), 3.02 (m, 1H), 2.91 (m, 2H).

EXAMPLE 7
(Method 3)

2-{2-[2-(1H-Indol-3-yl)-ethylamino]-3,4-dioxo-cyclobut-1-enylamino}-L-phenylalanine

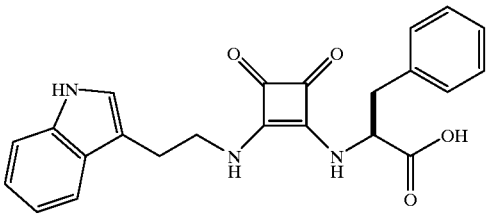

Following the procedure of Method 3 above, the title compound was obtained in 61% yield as a white solid.

$^1$H NMR (DMSO-$d_6$, 400 MHz) δ13.3 (br s, 1H), 10.8 (s, 1H), 7.58 (d, 2H, J=7.8 Hz), 7.32 (d, 1H, J=8.1 Hz), 7.10–7.30 (m, 6H), 7.06 (m, 1H), 6.97 (m, 1H), 4.90 (m, 1H), 3.79 (m, 2H), 3.38 (q, 1H, J=7.0 Hz), 3.14 (dd, 1H, J=13.9; 4.7 Hz), 3.01 (dd, 1H, J=13.9; 4.7 Hz), 2.92 (m, 2H).

MS (EI, m/e (%)) 403 (4, M$^+$), 385 (16), 294 (60), 143 (100).

Anal. Calc'd for $C_{23}H_{21}N_3O_4$.0.4 $H_2O$: C, 67.27; H, 5.35; N, 10.23.

Found: C, 67.58; H, 5.82; N, 9.78.

EXAMPLE 8
(Method 2)

2-{3,4-Dioxo-2-[(pyridin-3-ylmethyl)-amino]-cyclobut-1-enylamino}-3-phenyl-propionic acid methyl ester Following the procedure of Method 2 above, the title compound was obtained from [2-ethoxy-3,4-dioxocyclobut-1-enyl]-L-phenylalanine methyl ester and 3-pyridylmethylamine in 81% yield, mp=191–192° C.

$^1$H NMR (DMSO-d$_6$, 400 MHz) δ8.51 (d, 2H, J=5.1 Hz), 7.87 (br s, 1H), 7.68 (br s, 2H), 7.40 (dd, 1H, J=4.7, 7.6 Hz), 7.24 (m, 3H), 7.13 (d, 2H, J=7.2 Hz), 5.01 (br s, 1H), 4.72 (d, 2H, 5.7 Hz), 3.68 (s, 3H), 3.17 (dd, 1H, J=5.2, 13.7 Hz), 3.03 (m, 1H).

MS (EI, m/e (%)) 365 (6, M$^+$), 337 (7), 274 (15), 242 (40), 214 (18), 186 (13), 146 (44), 44 (100).

IR (KBr, cm$^{-1}$) 3175, 2960, 1800, 1745, 1650, 1570, 1480, 1430, 1310, 1280.

Anal. Calc'd for $C_{20}H_{19}N_3O_4$: C, 65.74; H, 5.24; N, 11.50.

Found: C, 65.22; H, 5.15; N, 11.27.

EXAMPLE 9

(Method 3)

{3,4-Dioxo-2-[(pyridin-3-ylmethyl)-amino]-cyclobut-1-enyl}-L-phenylalanine

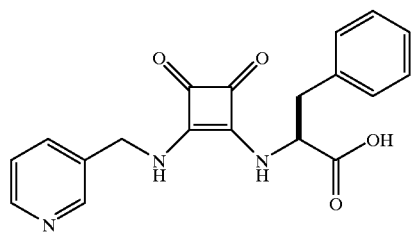

Following the procedure of Method 3 above, the title compound was obtained in 9% yield as a white solid, mp=259–261° C.

$^1$H NMR (DMSO-d$_6$, 300 MHz) δ13.25 (br s, 1H), 8.53 (br d, 2H) 7.93 (br s, 1H), 7.69 (br d, 2H), 7.41 (m, 1H), 7.20 (m, 5H), 4.91 (m, 1H), 4.73 (m, 2H), 3.18 (dd, 1H), 3.03 (m, 1H).

MS ((+) FAB, m/e (%)) 352 (10, (M+H)$^+$), 232 (17), 179 (23), 157 (100).

EXAMPLE 10

(Method 2)

[2-(Benzyl-hexyl-amino)-3,4-dioxo-cyclobut-1-enyl]-L-phenylalanine methyl ester

Following the procedure of Method 2 above, the title compound was obtained from [2-ethoxy-3,4-dioxo-cyclobut-1-enyl]-L-phenylalanine methyl ester and benzyl (hexyl)-amine in 57% yield as a light yellow oil which was carried on immediately to the subsequent reaction.

EXAMPLE 11

(Method 3)

[2-(Benzyl-hexyl-amino)-3,4-dioxo-cyclobut-1-enyl]-L-phenylalanine

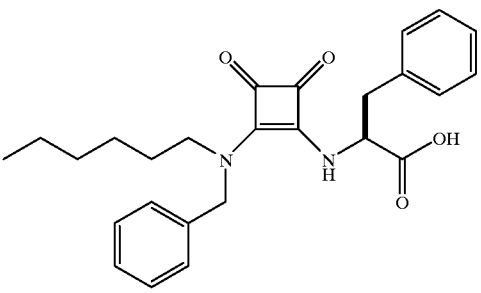

Following the procedure of Method 3 above, the title compound was obtained in 41% yield as a yellow foam, mp=61–65° C.

$^1$H NMR (DMSO-d$_6$, 400 MHz) δ13.1 (s, 1H), 7.79 (br s, 1H), 7.35 (dd, 3H, J=10.6, 6.9 Hz), 7.21 (m, 6H), 5.14 (m, 1H), 4.67 (br s, 2H), 3.38 (br m, 2H), 3.26 (dd, 2H, J=14, 4.0 Hz), 2.98 (dd, 1H, J=14.1, 11.2 Hz), 1.38 (br s, 2H), 1.15 (m, 6H), 0.82 (t, 3H, J=6.8 Hz).

MS ((+)FAB, m/e (%)) 457 (76, (M+Na)$^+$), 435 (100, (M+H)$^+$), 389 (13), 192 (35).

IR (KBr, cm$^{-1}$) 3290, 2940, 1800, 1740, 1675, 1570, 1520, 700.

Anal Calc'd for $C_{26}H_{30}N_2O_4$.0.25 H$_2$O; C, 71.13; H, 7.00; N, 6.38.

Found: C, 71.31; H, 7.00; N, 6.20.

EXAMPLE 12

(Method 2)

(2-Dibenzylamino-3,4-dioxo-cyclobut-1-enylamino)-L-phenylalanine methyl ester

Following the procedure of Method 2 above, the title compound was obtained from [2-ethoxy-3,4-dioxo-cyclobut-1-enyl]-L-phenylalanine methyl ester and dibenzylamine in 44% yield as a light yellow solid which was carried on immediately to the subsequent reaction.

EXAMPLE 13

(Method 3)

(2-Dibenzylamino-3,4-dioxo-cyclobut-1-enylamino)-L-phenylalanine

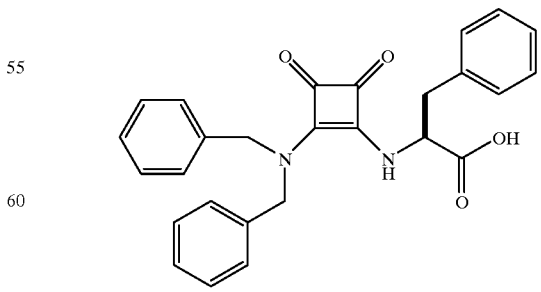

Following the procedure of Method 3 above, the title compound was obtained in 79% yield as a yellow solid.

$^1$H NMR (DMSO-d$_6$, 400 MHz) δ13.13 (s, 1H), 8.01 (d, 1H, J=9.0 Hz), 7.35 (m, 6H), 7.20 (m, 8H), 5.19 (m, 1H), 4.55 (br s, 4H), 3.26 (dd, 2H, J=3.9, 14.0 Hz), 2.97 (m, 1H).

MS (EI, m/e (%)) 440 (20, M$^+$), 349 (16), 91(100).

IR (KBr, cm$^{-1}$) 3450–3250 (br), 2925, 1800, 1740, 1680, 1570, 1520, 1445, 1265, 700.

Anal. Calc'd for C$_{27}$H$_{24}$N$_2$O$_4$: C, 73.62; H, 5.49; N, 6.36.

Found: C, 72.48; H, 5.41; N, 6.01.

EXAMPLE 14
(Method 2)

(S)-2-(2-Dihexylamino-3,4-dioxo-cyclobut-1-enylamino)-3-phenyl-propionic acid methyl ester Following the procedure of Method 2 above, the title compound was obtained from [2-ethoxy-3,4-dioxo-cyclobut-1-enyl]-L-phenylalanine methyl ester and dihexylamine in 62% yield as a light yellow solid which was carried on immediately to the subsequent reaction.

EXAMPLE 15
(Method 3)

(S)-2-(2-Dihexylamino-3,4-dioxo-cyclobut-1-enylamino)-3-phenyl-propionic acid

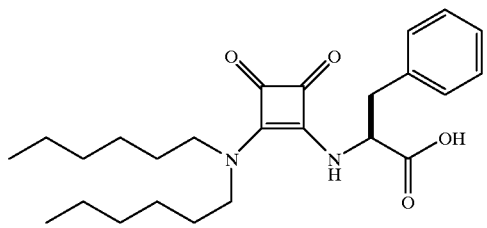

Following the procedure of Method 3 above, the title compound was obtained in 86% yield as a colorless oil.

$^1$H NMR (DMSO-d$_6$, 400 MHz) δ13.1 (br s, 1H), 7.58 (d, 1H, J=9.2 Hz), 7.2 (m, 5H), 5.09 (m, 1H), 3.44 (br s, 4H), 3.24 (dd, 1H, J=4.0, 13.8 Hz), 3.0 (dd, 1H, J=11.3, 14.1 Hz), 1.43 (br s, 4H), 1.20 (m, 12H), 0.84 (t, 6H, J=7.0 Hz).

MS (EI, m/e (%) 428 (100, M$^+$), 372 (36), 337 (55), 224 (30).

EXAMPLE 16
(Method 2)

(S)-2-[2-(Hexyl-naphthalen-2-ylmethyl-amino)-3,4-dioxo-cyclobut-1-enylamino]-3-phenyl-propionic acid methyl ester Following the procedure of Method 2 above, the title compound was obtained from [2-ethoxy-3,4-dioxo-cyclobut-1-enyl]-L-phenylalanine methyl ester and (2-naphthalenyl-methyl)hexylamine in 63% yield as a colorless oil which was carried on immediately to the subsequent reaction.

EXAMPLE 17
(Method 3)

(S)-2-[2-(Hexyl-naphthalen-2-ylmethyl-amino)-3,4-dioxo-cyclobut-1-enylamino]-3-phenyl-propionic acid

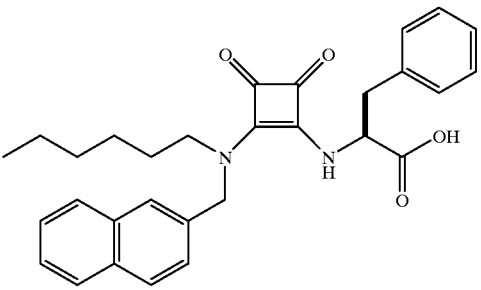

Following the procedure of Method 3 above, the title compound was obtained in 80% yield as a light yellow solid, mp=62–70° C.

$^1$H NMR (DMSO-d$_6$, 400 MHz) δ13.15 (br s, 1H), 7.91 (m, 2H), 7.80 (s, 1H), 7.52 (m, 2H), 7.29 (m, 2H) 7.21 (m, 6H), 5.17 (m, 1H), 4.84 (br s, 2H), 3.24 (dd, 2H, J=3.7, 14.3 Hz), 2.99 (m, 1H), 1.48–1.2 (m, 3H), 1.13 (s, 6H), 0.78 (t, 3H, J=6.7 Hz).

MS (EI, m/e (%)) 484 (5, M$^+$), 439 (4), 219 (28), 44 (100).

EXAMPLE 18
(Method 2)

(S)-2-{2-[(4-Dimethylamino-benzyl)-hexyl-amino]-3,4-dioxo-cyclobut-1-enylamino}-3-phenyl-propionic acid methyl ester Following the procedure of Method 2 above, the title compound was obtained from [2-ethoxy-3,4-dioxo-cyclobut-1-enyl]-L-phenylalanine methyl ester and (4-dimethyl-aminobenzyl)hexylamine in 59yield as a colorless oil which was carried on immediately to the subsequent reaction.

EXAMPLE 19
(Method 3)

(S)-2-{2-[(4-Dimethylamino-benzyl)-hexyl-amino]-3,4-dioxo-cyclobut-1-enylamino}-3-phenyl-propionic acid

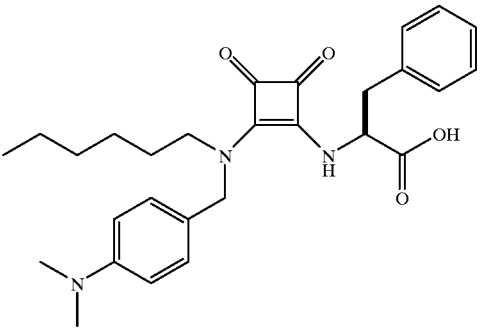

Following the procedure of Method 3 above, the title compound was obtained in 97% yield as a white solid, mp=77–80° C.

$^1$H NMR (DMSO-d$_6$, 400 MHz) δ13.07 (s, 1H), 7.78 (br s, 1H), 7.23 (m, 5H), 7.02 (br s, 2H), 6.65 (d, 2H, J=7.9 Hz), 5.16 (br s, 1H), 4.49 (br s, 2H), 3.26 (dd, 1H, J=3.7, 13.8 Hz), 3.0 (m, 1H), 2.87 (s, 6H), 1.48 (br s, 3H), 1.15 (m, 7H), 0.82 (t, 3H, J=6.8 Hz).

MS ((+)FAB, m/e (%)) 500 (100, [M+Na]$^+$), 478 (34, [M+H]$^+$), 455 (17), 357 (32).

EXAMPLE 20

(Method 2)

N-[3,4-Dioxo-2-(4-phenyl-piperazin-1-yl)-cyclobut-1-en-1-yl]-L-phenylalanine methyl ester Following the procedure of Method 2 above, the title compound was obtained from [2-ethoxy-3,4-dioxo-cyclobut-1-enyl]-L-phenylalanine methyl ester and 1-phenyl-piperazine in 63% yield as a white solid which was carried on immediately to the subsequent reaction.

EXAMPLE 21

(Method 3)

N-[3,4-Dioxo-2-(4-phenyl-piperazin-1-yl)-cyclobut-1-en-1-yl]-L-phenylalanine

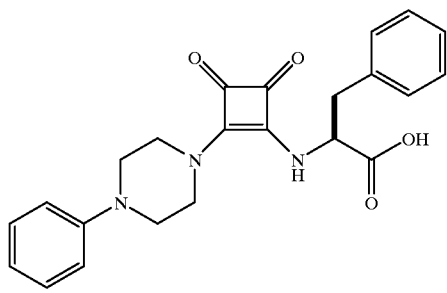

Following the procedure of Method 3 above, the title compound was obtained in 65% yield as a white solid, mp=165–167° C.

$^1$H NMR (DMSO-d$_6$, 400 MHz) δ13.1 (br s, 1H), 8.01 (d, 1H, J=9.0 Hz) 7.29–7.16 (m, 7H), 6.98 (d, 2H, J=8.1 Hz), 6.82 (t, 1H, J=7.2 Hz), 5.08 (m, 1H), 3.77 (br s, 4H), 3.24 (dd, 2H, J=4.0, 14.0 Hz), 3.19 (t, 3H, J=5.0 Hz), 2.98 (dd, 1H, J=11.0, 13.8 Hz).

MS (EI, m/e (%)) 405 (48, M$^+$), 361 (6), 304 (5), 44 (100).

EXAMPLE 22

(Method 2)

(S)-2-[2-(4-Acetyl-piperazin-1-yl)-3,4-dioxo-cyclobut-1-enylamino]-3-phenyl-propionic acid methyl ester Following the procedure of Method 2 above, the title compound was obtained from [2-ethoxy-3,4-dioxo-cyclobut-1-enyl]-L-phenylalanine methyl ester and 1-acetylpiperazine in 71% yield as a white solid which was carried on immediately to the subsequent reaction.

EXAMPLE 23

(Method 3)

(S)-2-[2-(4-Acetyl-piperazin-1-yl)-3,4-dioxo-cyclobut-1-enylamino]-3-phenyl-propionic acid

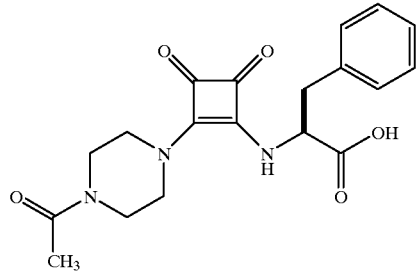

Following the procedure of Method 3 above, the title compound was obtained in 39% yield as a white solid, mp=155–158° C.

$^1$H NMR (DMSO-d$_6$, 400 MHz) δ13.1 (br s, 1H), 7.96 (d, 1H, J=9.2 Hz) 7.24 (m, 5H), 5.07 (m, 1H), 3.66 (br s, 2H), 3.57 (br s, 3H), 3.50 (d, 3H, J=4.2 Hz), 3.23 (dd, 1H, J=4.2, 13.8 Hz), 2.97 (dd, 1H, J=11.0, 13.8 Hz), 2.03 (s, 3H).

MS (EI, m/e (%)) 371 (21, M$^+$), 270 (10).

EXAMPLE 24

(Method 1)

[2-Ethoxy-3,4-dioxo-cyclobut-1-enyl]-L-(4-benzoylamino)phenylalanine methyl ester Following the procedure of Method 1 above, the title compound was obtained from L-(4-benzoylamino)phenylalanine methyl ester hydrochloride and 3,4-diethoxy-3-cyclobutene-1,2-dione in 64% yield.

$^1$H NMR (DMSO-d$_6$, 300 MHz) δ10.2 (s, 1H), 9.1 (br dd, 1H), 7.93 (dd, 2H), 7.69 (d, 2H), 7.53 (m, 3H), 7.2 (d, 2H), 4.59 (m, 3H), 3.7 (s, 3H), 3.21 (dd, 1H), 2.93 (br m, 1H), 1.31 (m, 3H).

EXAMPLE 25

(Method 2)

(S)-3-(4-Benzoylamino-phenyl)-2-(2-dihexylamino-3,4-dioxo-cyclobut-1-enylamino)-propionic acid methyl ester Following the procedure of Method 2 above, the title compound was obtained from [2-ethoxy-3,4-dioxo-cyclobut-1-enyl]-L-(4-benzoylamino)phenylalanine methyl ester and dihexylamine in 70% yield as a white solid which was carried on immediately to the subsequent reaction.

EXAMPLE 26

(Method 3)

(S)-3-(4-Benzoylamino-phenyl)-2-(2-dihexylamino-3,4-dioxo-cyclobut-1-enylamino)-propionic acid

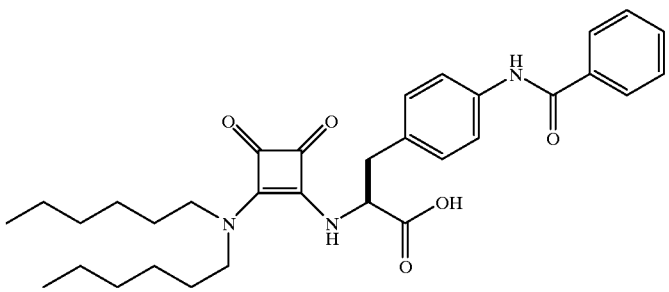

Following the procedure of Method 3 above, the title compound was obtained in 61% yield as a white solid, mp=95–100° C.

$^1$H NMR (DMSO-d$_6$, 400 MHz) δ13.1 (br s, 1H), 10.17 (s, 1H), 7.91 (m, 2H), 7.68 (d, 2H, J=8.6 Hz), 7.6–7.48 (m, 4H), 7.19 (d, 2H, J=8.6 Hz), 5.09 (m, 1H), 3.45 (br m, 4H), 3.22 (dd, 1H, J=3.8, 13.9 Hz), 2.98 (dd, 1H, J=11.2, 13.8 Hz), 1.43 (br s, 4H), 1.20 (s, 12H), 0.80 (t, 6H, J=6.7 Hz).

MS ((+)FAB, m/e (%)) 570 (51, [M+Na]$^+$), 548 (25, [M+H]$^+$), 210 (10), 105 (100).

Anal. Calc'd for C$_{32}$H$_{41}$N$_3$O$_5$.0.4 H$_2$O: C, 69.26; H, 7.59; N, 7.57.

Found: C, 69.14; H, 7.55; N, 7.52.

EXAMPLE 27

(Method 1)

2-Ethoxy-3,4-dioxo-cyclobut-1-enyl]-L-(im-benzyl) histidine methyl ester

Following the procedure of Method 1 above, the title compound was obtained from L-(im-benzyl)histidine methyl ester hydrochloride and 3,4-diethoxy-3-cyclobutene-1,2-dione in 58% yield.

$^1$H NMR (DMSO-d$_6$, 300 MHz) δ9.0 (br dd, 1H), 7.67 (s, 1H), 7.31 (m, 3H), 7.16 (d, 2H), 6.91 (br s, 1H), 5.12 (s, 2H), 4.6 (m, 3H), 3.62 (d, 3H), 3.05 (dd, 1H), 2.9 (m, 1H), 1.3 (m, 3H).

EXAMPLE 28

(Method 2)

(S)-3-(1-Benzyl-1H-imidazol-4-yl)-2-(2-dihexylamino-3,4-dioxo-cyclobut-1-enylamino)-propionic acid methyl ester Following the procedure of Method 2 above, the title compound was obtained from [2-ethoxy-3,4-dioxo-cyclobut-1-enyl]-L-(im-benzyl)histidine methyl ester and dihexylamine in 94% yield as a white solid which was carried on immediately to the subsequent reaction.

EXAMPLE 29

(Method 3)

(S)-3-(1-Benzyl-1H-imidazol-4-yl)-2-(2-dihexylamino-3,4-dioxo-cyclobut-1-enylamino)-propionic acid

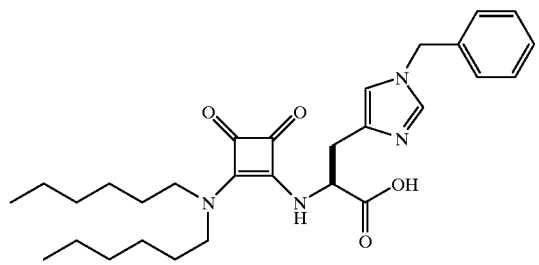

Following the procedure of Method 3 above, the title compound was obtained in 45% yield as a white solid, mp=75–80° C.

$^1$H NMR (DMSO-d$_6$, 400 MHz) δ7.87 (d, J=8.8 Hz, 1H); 7.66 (s, 1H), 7.29 (m, 3H), 7.16 (dd, J=6.4, 1.8 Hz, 2H), 6.92 (s, 1H), 5.13 (s, 2H), 5.04 (q, J=8.3, 5.8 Hz, 1H), 3.55 (br, 4H), 3.01 (m, 2H), 1.49 (br s, 4H), 1.21 (s, 13H), 0.82 (s, 6H).

MS ((+)FAB, m/e (%)) 509 (100, [M+H]$^+$), 185 (30), 172 (40).

Anal. Calc'd for C$_{29}$H$_{40}$N$_4$O$_4$.0.5 H$_2$O: C, 67.28; H, 7.98; N, 10.82.

Found: C, 67.53; H, 8.10; N, 10.47.

EXAMPLE 30

(Method 1)

[2-Ethoxy-3,4-dioxo-cyclobut-1-enyl]-O-(3-dimethylaminopropyl)-L-tyrosine methyl ester Following the procedure of Method 1 above, the title compound was obtained from O-(3-dimethylaminopropyl)-L-tyrosine methyl ester hydrochloride and 3,4-diethoxy-3-cyclobutene-1,2-dione in 71% yield.

$^1$H NMR (DMSO-d$_6$, 300 MHz) δ9.1 (br d, 1H), 7.12 (d, 2H), 6.82 (d, 2H), 4.89 (m, 1H), 4.6 (m, 2H), 3.93 (t, 2H), 3.69 (s, 3H), 3.1 (m, 1H), 2.88 (m, 1H), 2.31 (t, 2H), 2.12 (s, 6H), 1.8 (m, 2H), 1.3 (m, 3H).

EXAMPLE 31

(Method 2)

N-(2-Dihexylamino-3,4-dioxo-cyclobut-1-enylamino)-O-(3-dimethylamino-propyl)-L-tyrosine methyl ester Following the procedure of Method 2 above, the title compound was obtained from [2-ethoxy-3,4-dioxocyclobut-1-enyl]-O-(3-dimethylaminopropyl)-L-tyrosine methyl ester and dihexylamine in 23% yield as a white solid which was carried on immediately to the subsequent reaction.

EXAMPLE 32
(Method 3 (Modified))

N-(2-Dihexylamino-3,4-dioxo-cyclobut-1-enylamino)-O-(3-dimethylamino-propyl)-L-tyrosine

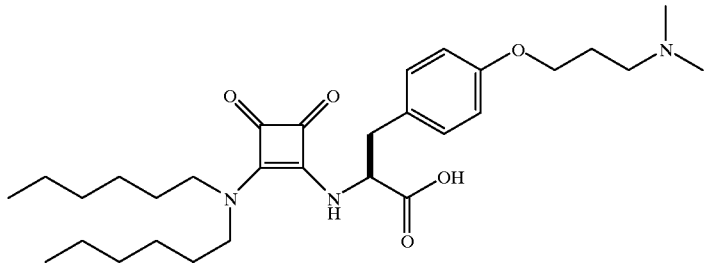

Following a modification procedure of Method 3 above, the lithium salt of the title compound was obtained in 66% yield as a light yellow solid. The modified procedure requires removing the volatiles in vacuo from the reaction mixture following completion of ester hydrolysis (usually 3 hours at room temperature), followed by partitioning the reaction mixture between EtOAc and water. The aqueous phase is then lyophilized to afford the lithium salt as an amorphous powder.

$^1$H NMR (DMSO-d$_6$, 400 MHz) δ7.08 (d, 1H, J=6.6 Hz), 6.95 (d, 2H, J=8.6 Hz), 6.68 (d, 2H, J=8.6 Hz), 4.28 (m, 1H), 3.87 (t, 2H, J=6.4 Hz), 3.3 (br s, 4H), 3.05 (d, 2H, J=5.1 Hz) 2.31 (t, 2H, J=7.1 Hz), 2.11 (s, 6H), 1.78 (t, 2H, J=6.9 Hz), 1.43 (br s, 4H), 1.19 (br m, 12H), 0.82 (t, 6H, J=7.0 Hz).

MS ((+)FAB, m/e (%)) 536 (100, [M+Li]$^+$), 530 (50, [M+H]$^+$).

IR (KBr, cm$^{-1}$) 3400, 2960, 2930, 2880, 1800, 1575, 1520, 1240.

EXAMPLE 33
(Method 1)

[2-Ethoxy-3,4-dioxo-cyclobut-1-enyl]-4-[(4-pyridinylcarbonyl)amino]-L-phenylalanine methyl ester Following the procedure of Method 1 above, the title compound was obtained from 4-[(4-pyridinylcarbonyl) amino]-L-phenylalanine methyl ester hydrochloride and 3,4-diethoxy-3-cyclobutene-1,2-dione in 71% yield.

$^1$H NMR (DMSO-d$_6$, 300 MHz) δ10.47 (s, 1H), 9.12 (br dd, 1H), 8.78 (dd, 2H), 7.83 (d, 2H), 7.69 (d, 2H), 7.23 (d, 2H), 4.9 (br m, 1H), 4.59 (m, 2H), 3.7 (s, 3H), 3.22 (dd, 1H), 2.94 (m, 1H), 1.31 (m, 3H).

EXAMPLE 34
(Method 2)

N-[2-[Methyl[2-(4-pyridinyl)ethyl]amino]-3,4-dioxo-1-cyclobuten-1-yl]-4-[(4-pyridinylcarbonyl) amino]-L-phenylalanine methyl ester Following the procedure of Method 2 above, the title compound was obtained from [2-ethoxy-3,4-dioxo-cyclobut-1-enyl]-4-[(4-pyridinylcarbonyl)amino]-L-phenylalanine methyl ester and methyl-[2-(4-pyridinyl) ethyl]amine in 41% yield as a yellow foam which was carried on immediately to the subsequent reaction.

EXAMPLE 35
(Method 3 (Modified))

N-[2-[Methyl[2-(4-pyridinyl)ethyl]amino]-3,4-dioxo-1-cyclobuten-1yl]-4-[(4-pyridinylcarbonyl) amino]-L-phenylalanine

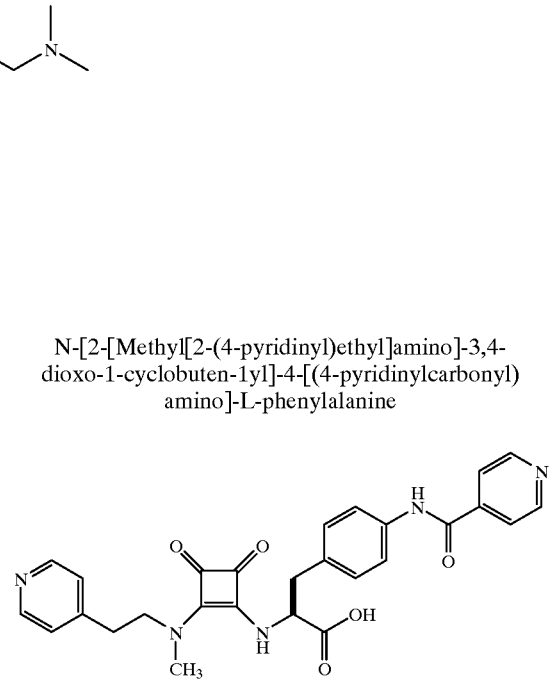

Following the procedure of Method 3 (modified) above, the title compound was obtained as its corresponding lithium salt in 73% yield as a yellow solid.

$^1$H NMR (DMSO-d$_6$, 400 MHz) δ10.45 (s, 1H), 8.74 (dd, J=1.5, 4.6 Hz, 2H), 8.40 (d, J=4.8 Hz, 2H), 7.81 (d, J=6.1 Hz, 2H), 7.59 (d, J=8.3 Hz, 2H), 7.40 (br m, 1H), 7.20 (d, J=5.3 Hz, 2H), 7.10 (d, J=8.3 Hz, 2H), 4.40 (m, 1H), 3.70 (br s, 2H), 3.10 (m, 6H), 2.81 (m, 2H).

MS ((+)FAB, m/e (%)) 506 (100, [M+Li]$^+$), 500 (50, [M+H]$^+$).

IR (KBr, cm$^{-1}$) 3400, 1575, 1530, 1410, 1320.

Anal. Calc'd for $C_{27}H_{24}N_5O_5Li.3.5 H_2O$: C, 56.98; H, 5.49; N, 12.31.

Found: C, 56.96; H, 5.34; N, 11.82.

EXAMPLE 36
(Method 2)

N-[2-[Methyl(2-phenylethyl)amino]-3,4-dioxo-1-cyclobuten-1-yl]-4-[(4-pyridinylcarbonyl)amino]-L-phenylalanine methyl ester Following the procedure of Method 2 above, the title compound was obtained from [2-ethoxy-3,4-dioxo-cyclobut-1-enyl]-4-[(4-pyridinylcarbonyl)amino]-L-phenylalanine methyl ester and methyl-(2-phenyl)amine in 93% yield as a colorless foam which was carried on immediately to the subsequent reaction.

EXAMPLE 37
(Method 3 (Modified))

N-[2-[Methyl(2-phenylethyl)amino]-3,4-dioxo-1-cyclobuten-1-yl]-4-[(4-pyridinylcarbonyl)amino]-L-phenylalanine

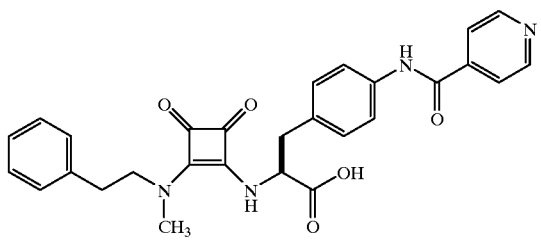

Following the procedure of Method 3 (modified) above, the title compound was obtained as its corresponding lithium salt in 90% yield as a white solid.

$^1$H NMR (DMSO-$d_6$, 400 MHz) δ10.45 (s, 1H), 8.73 (m, 2H), 7.80 (d, J=5.7 Hz, 2H), 7.60 (d, J=8.6 Hz, 2H), 7.32–7.08 (m, 8H), 4.38 (d, J=4.6 Hz, 1H), 3.67 (br s, 2H), 3.08 (m, 5H), 2.79 (m, 2H).

MS ((+)FAB, m/e (%)) 521 (100, [M+Na]$^+$), 505 (85, [M+Li]$^+$), 499 (60, [M+H]$^+$).

IR (KBr, cm$^{-1}$) 3400, 1810, 1660, 1580, 1530, 1410, 1330.

EXAMPLE 38
(Method 2)

N-[2-(Dihexylamino)-3,4-dioxo-1-cyclobuten-1-yl]-4-[(4-pyridinylcarbonyl)amino]-L-phenylalanine methyl ester Following the procedure of Method 2 above, the title compound was obtained from [2-ethoxy-3,4-dioxo-cyclobut-1-enyl]-4-[(4-pyridinylcarbonyl)amino]-L-phenylalanine methyl ester and dihexylamine in 87% yield as a light yellow foam which was carried on immediately to the subsequent reaction.

EXAMPLE 39
(Method 3 (Modified))

N-[2-(Dihexylamino)-3,4-dioxo-1-cyclobuten-1-yl]-4-[(4-pyridinylcarbonyl)amino]-L-phenylalanine

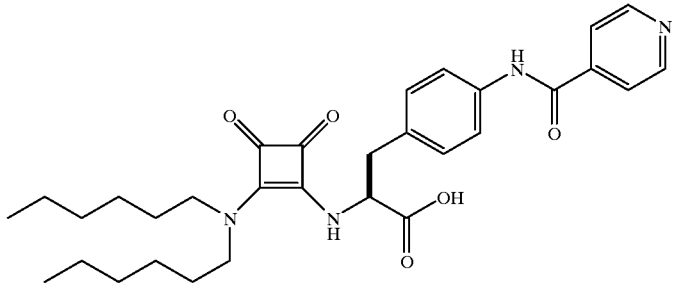

Following the procedure of Method 3 (modified) above, the title compound was obtained as its corresponding lithium salt in 92% yield as a white solid.

$^1$H NMR (DMSO-$d_6$, 400 MHz) δ10.46 (s, 1H), 8.75 (dd, J=4.4, 1.8 Hz, 2H), 7.83 (dd, J=4.4, 1.8 Hz, 2H), 7.61 (d, J=8.6 Hz, 2H), 7.11 (d, J=6.2 Hz, 1H), 7.05 (d, J=8.6 Hz, 2H), 4.33 (q, J=5.5 Hz, 1H), 3.65 (br s, 2H), 3.25 (br s, 2H), 3.11 (d, J=5.7 Hz, 3H), 1.43 (br s, 4H), 1.15 (br s, 11 Hz), 0.78 (s, 6H).

MS ((+)FAB, m/e (%)) 555 (100, [M+Li]$^+$), 549 (97, [M+H]$^+$).

IR (KBr, cm$^{-1}$) 3330, 2910, 1800, 1660, 1580, 1520, 1410, 1300.

Anal. Calc'd for $C_{31}H_{39}N_4O_5Li.2 H_2O$: C, 62.99; H, 7.33; N, 9.48.

Found: C, 62.65; H, 7.23; N, 9.31.

EXAMPLE 40
(Method 2)

N-[2-(Methyl-pyridin-3-ylmethyl-amino)-3,4-dioxo-cyclobut-1-enyl]-4-[(pyridine-4-carbonyl)-amino]-L-phenylalanine methyl ester Following the procedure of Method 2 above, the title compound was obtained from [2-ethoxy-3,4-dioxo-cyclobut-1-enyl]-4-[(4-pyridinylcarbonyl)amino]-L-phenylalanine methyl ester and methyl-(3-pyridinylmethyl)amine in 88% yield as a colorless foam which was carried on immediately to the subsequent reaction.

EXAMPLE 41
(Method 3 (Modified))

N-[2-(Methyl-pyridin-3-ylmethyl-amino)-3,4-dioxo-cyclobut-1-enyl]-4-[(pyridine-4-carbonyl)-amino]-L-phenylalanine

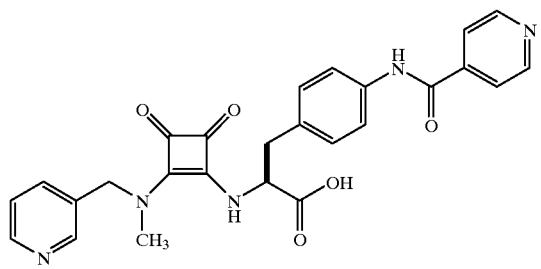

Following the procedure of Method 3 (modified) above, the title compound was obtained as its corresponding lithium salt in 85% yield as a yellow solid.

$^1$H NMR (DMSO-$d_6$, 400 MHz) δ10.47 (s, 1H), 8.77 (dd, J=4.4, 1.8 Hz, 2H), 8.50 (m, 2H), 7.84 (m, 2H), 7.70 (br m, 1H), 7.58 (d, J=8.6 Hz, 3H), 7.39 (dd, J=7.6, 4.9 Hz, 1H), 7.11 (d, J=8.3 Hz, 2H), 4.7 (d, J=15.2 Hz, 1H), 4.68 (br m, 1H), 4.54 (br s, 1H), 3.18 (dd, J=13.6, 4.3 Hz, 1H), 3.01 (s, 3H), 2.94 (dd, J=13.6, 8.3 Hz, 1H).

MS ((+), (−) ESI, m/e (%)) 486 (82, [M+H]$^+$), 484 (58, [M−H]$^-$).

IR (KBr, cm$^{-1}$) 3400, 1800, 1620, 1580, 1530, 1410, 1325.

EXAMPLE 42
(Method 1)

[2-Ethoxy-3,4-dioxo-cyclobut-1-enyl]-4-[(3-pyridinylcarbonyl)amino]-L-phenylalanine methyl ester Following the procedure of Method 1 above, the title compound was obtained from 4-[(3-pyridinylcarbonyl) amino]-L-phenylalanine methyl ester hydrochloride and 3,4-diethoxy-3-cyclobutene-1,2-dione in 74% yield.

$^1$H NMR (DMSO-d$_6$, 300 MHz) δ10.4 (s, 1H), 9.1 (br dd, 1H), 9.08 (d, 1H) 8.75 (dd, 1H), 8.27 (dt, 1H), 7.68 (d, 2H), 7.56 (dd, 1H), 7.23 (d, 2H), 4.9 (m, 1H), 4.58 (m, 2H), 3.68 (s, 3H), 3.23 (dd, 1H), 2.96 (m, 1H), 1.32 (m, 3H).

EXAMPLE 43
(Method 2)

N-[2-(Dihexylamino)-3,4-dioxo-1-cyclobuten-1-yl]-4-[(3-pyridinylcarbonyl)amino]-L-phenylalanine methyl ester Following the procedure of Method 2 above, the title compound was obtained from [2-ethoxy-3,4-dioxo-cyclobut-1-enyl]-4-[(3-pyridinylcarbonyl)amino]-L-phenylalanine methyl ester and dihexylamine in 95% yield as a yellow foam which was carried on immediately to the subsequent reaction.

EXAMPLE 44
(Method 3 (Modified))

N-[2-(Dihexylamino)-3,4-dioxo-1-cyclobuten-1-yl]-4-[(3-pyridinylcarbonyl)amino]-L-phenylalanine Following the procedure of Method 3 (modified) above, the title compound was obtained as its corresponding lithium salt in 53% yield as a white solid.

$^1$H NMR (DMSO-d$_6$, 400 MHz) δ10.38 (s, 1H), 9.06 (dd, J=2.4, 1.8 Hz, 1H), 8.72 (dd, J=4.7, 1.7 Hz, 1H), 8.25 (dt, J=2.0 Hz, 1H), 7.60 (d, J=8.6 Hz, 2H), 7.54 (m, 1H), 7.09 (d, J=6.4 Hz, 1H), 7.04 (d, J=8.6 Hz, 2H), 4.45 (m, 1H), 3.28 (br s, 4H), 3.11 (dd, J=13.6, 4.8 Hz, 1H), 2.99 (dd, J=13.8, 7.2 Hz, 1H), 1.40 (br s, 4H), 1.16 (br s, 12H), 0.74 (s, 6H).

MS ((+)FAB, m/e (%)) 555 (43, [M+Li]$^+$), 549 (100, [M+H]$^+$).

IR (KBr, cm$^{-1}$) 3375 (br), 2900, 1800, 1660, 1575, 1530, 1410, 1325.

EXAMPLE 45
(Method 2)

N-[2-[Methyl[2-(4-pyridinyl)ethyl]amino]-3,4-dioxo-1-cyclobuten-1-yl]-4-[(3-pyridinylcarbonyl) amino]-L-phenylalanine methyl ester Following the procedure of Method 2 above, the title compound was obtained from [2-ethoxy-3,4-dioxo-cyclobut-1-enyl]-4-[(3-pyridinylcarbonyl)amino]-L-phenylalanine methyl ester and methyl-[2-(4-pyridinyl) ethyl]amine in 54% yield as a yellow foam which was carried on immediately to the subsequent reaction.

EXAMPLE 46
(Method 3 (Modified))

N-[2-[Methyl[2-(4-pyridinyl)ethyl]amino]-3,4-dioxo-1-cyclobuten-1-yl]-4-[3-pyridinylcarbonyl) amino]-L-phenylalanine Following the procedure of Method 3 (modified) above, the title compound was obtained as its corresponding lithium salt in 81% yield as a pale yellow solid.

$^1$H NMR (DMSO-d$_6$, 400 MH) δ10.39 (s, 1H), 9.04 (d, J=1.8 Hz, 1H), 8.71 (dd, J=4.8, 1.8 Hz, 1H), 8.39 (d, J=4.6 Hz, 2H), 8.24 (d, J=8.1 Hz, 1H), 7.58 (d, J=8.3 Hz, 2H), 7.52 (m, 1H), 7.43 (br s, 1H), 7.19 (d, J=5.3 Hz, 2H), 7.10 (d, J=8.6 Hz, 2H), 4.42 (d, J=4.4 Hz, 1H), 3.70 (br s, 2H), 3.10 (m, 5H), 2.81 (m, 2H).

MS ((+)ESI, m/e (%)) 506 (25, [M+Li]$^+$), 500 (100, [M+H]$^+$).

IR (KBr, cm$^{-1}$) 3400 (br), 1810, 1660, 1580, 1535, 1410, 1320.

Anal. Calc'd for $C_{27}H_{24}N_5O_5Li.2.5\ H_2O$: C, 58.90; H, 5.49; N, 12.72.

EXAMPLE 47
(Method 2)

N-[2-(Methyl-pyridin-3-ylmethyl-amino)-3,4-dioxo-cyclobut-1-enyl]-4-[(pyridine-3-carbonyl)-amino]-L-phenylalanine methyl ester Following the procedure of Method 2 above, the title compound was obtained from [2-ethoxy-3,4-dioxo-cyclobut-1-enyl]-4-[(3-pyridinylcarbonyl)amino]-L-phenylalanine methyl ester and methyl-(3-pyridinylmethyl) amine in 66% yield as a colorless foam which was carried on immediately to the subsequent reaction.

EXAMPLE 48
(Method 3 (Modified))

N-[2-(Methyl-pyridin-3-ylmethyl-amino)-3,4-dioxo-cyclobut-1-enyl]-4-[(pyridine-3-carbonyl)-amino]-L-phenylalanine

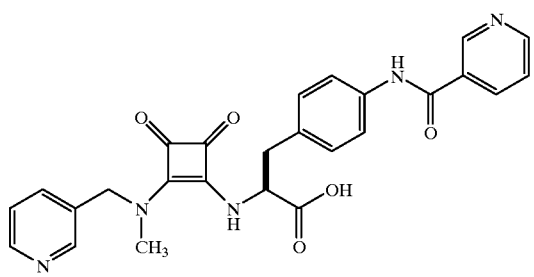

Following the procedure of Method 3 (modified) above, the title compound was obtained as its corresponding lithium salt in 73% yield as a white solid.

$^1$H NMR (DMSO-d$_6$, 400 MHz) δ10.4 (s, 1H), 9.08 (d, J=2.2 Hz, 1H), 8.73 (dd, J=4.8, 1.8 Hz, 1H), 8.5 (m, 2H), 8.28 (dt, J=2.0 Hz, 1H), 7.72 (br m, 1H), 7.57 (m, 4H), 7.39 (dd, J=7.7, 4.8 Hz, 1H), 7.12 (d, J=8.6 Hz, 2H), 4.76 (d, J=14.9 Hz, 1H), 4.66 (br m, 1H), 4.55 (br s, 1H), 3.18 (dd, J=13.6, 4.3 Hz, 1H), 3.01 (s, 3H), 2.94 (dd, J=13.8, 8.2 Hz, 1H).

MS ((−), (+)ESI, m/e (%)) 486 (18, [M+H]$^+$), 484 (100, [M-H]$^−$)

IR (KBr, cm$^{-1}$) 3275 (br), 1800, 1660, 1580, 1530, 1410, 1315.

Anal. Calc'd for C$_{26}$H$_{22}$N$_5$O$_5$Li.2.8 H$_2$O: C, 57.62; H, 5.13; N, 12.92.

Found: C, 57.56; H, 4.74; N, 12.73.

EXAMPLE 49
(Method 2)

N-{2-[Methyl-(2-pyridin-4-yl-ethyl)-amino]-3,4-dioxo-cyclobut-1-enyl}-L-phenylalanine methyl ester Following the procedure of Method 2 above, the title compound was obtained from [2-ethoxy-3,4-dioxo-cyclobut-1-enyl]-L-phenylalanine methyl ester and methyl-[2-(4-pyridinyl)ethyl]amine in 55% yield as a clear oil which was carried on immediately to the subsequent reaction.

EXAMPLE 50
(Method 3 (Modified))

N-{2-[Methyl-(2-pyridin-4-yl-ethyl)-amino]-3,4-dioxo-cyclobut-1-enyl}-L-phenylalanine

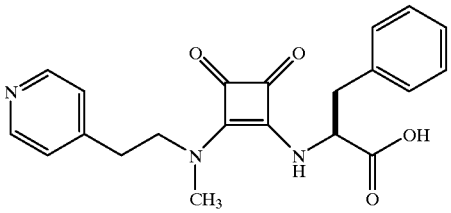

Following the procedure of Method 3 (modified) above, the title compound was obtained as its corresponding lithium salt in 87% yield as a white solid.

$^1$H NMR (DMSO-d$_6$, 400 MHz) δ8.4 (d, J=5.7 Hz, 2H), 7.42 (br m, 1H), 7.2 (d, J=5.7 Hz, 2H), 7.11 (m, 5H), 4.39 (d, J=4.6 Hz, 1H), 3.68 (br s, 2H), 3.18 (m, 5H), 2.78 (m, 2H).

MS ((+)FAB, m/e (%)) 402 (45, [M+Na]$^+$), 380 (100, [M+H]$^+$).

IR (KBr, cm$^{-1}$) 3375, 1800, 1580, 1530, 1410.

Anal. Calc'd for C$_{21}$H$_{20}$N$_3$O$_4$Li.1.5 H$_2$O: C, 61.21; H, 5.63; N, 10.20.

Found: C, 61.00; H, 5.44; N, 10.05.

EXAMPLE 51
(Method 1)

[2-Ethoxy-3,4-dioxo-cyclobut-1-enyl]-{4-[4-(N-carboxybenzoyl)piperidinylcarbonyl]amino}-L-phenylalanine methyl ester Following the procedure of Method 1 above, the title compound was obtained from {4-[4-(N-carboxybenzoyl)piperidinylcarbonyl]amino}-L-phenylalanine methyl ester hydrochloride and 3,4-diethoxy-3-cyclobutene-1,2-dione in 37% yield.

EXAMPLE 52
(Method 2)

N-[2-(Dihexylamino)-3,4-dioxo-1-cyclobuten-1-yl]-{4-[4-(N-carboxybenzoyl)piperidinylcarbonyl]amino}-L-phenylalanine methyl ester Following the procedure of Method 2 above, the title compound was obtained from [2-ethoxy-3,4-dioxo-cyclobut-1-enyl]-{4-[4-(N-carboxybenzoyl)piperidinylcarbonyl]-amino}-L-phenylalanine methyl ester and dihexylamine in 50% yield as a clear oil which was carried on immediately to the subsequent reaction.

EXAMPLE 53
(Method 3)

N-[2-(Dihexylamino)-3,4-dioxo-1-cyclobuten-1-yl]-{4-[4-(N-carboxybenzoyl)piperidinylcarbonyl]amino}-L-phenylalanine methyl ester Following the procedure of Method 3 above, the title compound was obtained in 75% yield as a light yellow solid, mp=75–80° C.

$^1$H NMR (DMSO-d$_6$, 400 MHz) δ13.01 (br s, 1H), 9.83 (s, 1H), 7.57 (d, 1H, J=9.0 Hz), 7.47 (d, 2H, J=8.3 Hz), 7.33 (m, 4H), 7.12 (d, 2H, J=8.6 Hz), 5.07 (s, 2H), 5.03 (m, 1H), 4.04 (d, 2H, J=13.2 Hz), 3.5 (br m, 4H), 3.28 (br s, under H$_2$O, 1H), 3.16 (dd, 1H, J=3.8 Hz), 2.93 (dd, 1H, J=11.0 Hz), 2.85 (br m, 2H), 1.76 (m, 2H), 1.48 (m, 6H), 1.20 (br s, 13H), 0.82 (t, 6H, J=6.7 Hz).

MS ([M+H]$^+$, m/e (%)) 689 (30), 555 (25), 186 (65), 91 (100).

IR (KBr, cm$^{-1}$) 3320, 2930, 1810, 1675, 1580, 1520, 1235.

Anal. Calc'd for C$_{39}$H$_{52}$N$_4$O$_7$. C, 68.00; H, 7.61; N, 8.13. Found: C, 67.60; H, 7.79; N, 7.95.

EXAMPLE 54
(Method 1)

[2-Ethoxy-3,4-dioxo-cyclobut-1-enyl]-L-tyrosine methyl ester

Following the procedure of Method 1 above, the title compound was obtained from L-tyrosine methyl ester hydrochloride and 3,4-diethoxy-3-cyclobutene-1,2-dione in 95% yield.

EXAMPLE 55
(Method 4)

(2S)-3-(4-Dimethylcarbamoyloxy-phenyl)-2-ethoxy-3,4-dioxo-cyclobut-1-enylamino]-propionic acid methyl ester To a solution of [2-ethoxy-3,4-dioxo-cyclobut-1-enyl]-L-tyrosine methyl ester (1.6 mmol, 500 mg) in pyridine (15 mL) was added neat dimethylcarbamyl chloride (4.7 mmol, 505 mg; 433 µL) dropwise and the resulting solution was heated at 40° C. for 18 hours. The volatiles were removed in vacuo and the residue was partitioned between EtOAc and 1N HCl. The organics were washed with additional 1N HCl, water, and brine and dried (Na$_2$SO$_4$). Purification by flash chromatography (SiO$_2$:60% EtOAc/hexane) afforded the title compound as a yellow foam (282 mg; 45% yield).

EXAMPLE 56
(Method 2)

(2S)-3-(4-Dimethylcarbamoyloxy-phenyl)-2-[2-(methyl-phenethyl-amino)-3,4-dioxo-cyclobut-1-ethylamino]-propionic acid methyl ester Following the procedure of Method 2 above, the title compound was obtained from (2S)-3-(4-dimethylcarbamoyloxy-phenyl)-2-ethoxy-3,4-dioxo-cyclobut-1-enylamino]-propionic acid methyl ester and methyl-(2-phenethyl)amine in 75% yield as a colorless foam which was carried on immediately to the subsequent reaction.

$^1$H NMR (DMSO-d$_6$, 400MHz) δ7.85 (d, 1H, J=9.0 Hz), 7.22 (m, 8H), 7.01 (d, 2H, J=8.6 Hz), 5.12 (m, 1H), 3.72 (br m, 1H), 3.68 (s, 3H), 3.21 (dd, 1H, J=4.5 Hz), 3.09 (s, 3H), 2.99 (s, 4H), 2.88 (s, 3H), 2.81 (m, 2H).

EXAMPLE 57
(Method 3 (Modified))

(2S)-3-(4-Dimethylcarbamoyloxy-phenyl-2-[2-(methyl-phenethyl-amino)-3,4-dioxo-cyclobut-1-enylamino]-propionic acid Following the procedure of Method 3 (modified) above, the title compound was obtained as its corresponding lithium salt in 82% yield as a white solid.

$^1$H NMR (DMSO-d$_6$, 400 MHz) δ7.33 (br m, 1H), 7.26 (m, 5H), 7.1 (d, 2H, J=8.6 Hz), 6.88 (d, 2H, J=8.6 Hz), 4.36 (d, 1H, J=4.8 Hz), 3.65 (br m, 2H), 3.12 (dd, 2H, J=5.1 Hz), 3.07 (s, 3H), 2.98 (s, 3H), 2.86 (s, 3H), 2.79 (m, 2H).

MS ((+)FAB, m/e (%)) 488 (55, [M+Na]$^+$), 472 (60, [M+Li]$^+$), 466 (100, [M+H]$^+$).

IR (KBr, cm$^{-1}$) 3410, 2910, 1810, 1725, 1580, 1530, 1410, 1210.

Anal. Calc'd for C$_{25}$H$_{26}$N$_3$O$_6$Li.1.5 H$_2$O. C, 60.24; H, 5.86; N, 8.43.

Found: C, 60.40; H, 5.65; N, 8.27.

EXAMPLE 58
(Method 2)

(2S)-2-(2-Dihexylamino-3,4-dioxo-cyclobut-1-enylamino)-3-(4-dimethylcarbamoyloxy-phenyl)-propionic acid methyl ester Following the procedure of Method 2 above, the title compound was obtained from (2S)-3-(4- dimethylcarbamoyloxy-phenyl)-2-ethoxy-3,4-dioxo-cyclobut-1-enylamino]-propionic acid methyl ester and dihexylamine in 40% yield as a yellow oil which was carried on immediately to the subsequent reaction.

EXAMPLE 59

(Method 3)

(2S)-2-(2-Dihexylamino-3,4-dioxo-cyclobut-1-enylamino)-3-(4-dimethylcarbamoyloxy-phenyl)-propionic acid

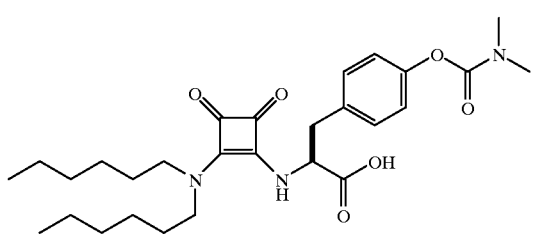

Following the procedure of Method 3 (modified) above, the title compound was obtained as its corresponding lithium salt in 70% yield as a light yellow solid.

$^1$H NMR (DMSO-d6, 400 MHz) δ7.11 (d, 1H, J=6.4 Hz), 7.045 (m, 2H), 6.87 (m, 2H), 4.28 (m, 1H), 3.5 (br m, 4H), 3.12 (d, 2H, J=5.3 Hz), 2.99 (s, 3H), 2.87 (s, 3H), 1.43 (br m, 4H), 1.18 (br m, 12H), 0.82 (t, 6H, J=6.9 Hz).

MS ((+)ESI, m/e (%)) 533 (30, (M+NH4$^+$)$^+$), 516 (100, (M+H)$^+$).

IR (KBr, cm$^{-1}$) 3400, 2910, 1800, 1730, 1580, 1520, 1380, 1220.

Anal. Calc'd for $C_{28}H_{40}N_3O_6Li \cdot 1.25\ H_2O$: C, 61.77; H, 7.87; N, 7.72.

Found: C, 61.67; H, 7.42; N, 7.45.

EXAMPLE 60

(Method 2)

(2S)-3-(4-Dimethylcarbamoyloxy-phenyl)-2-[2-(methyl-pyridin-3-ylmethyl-amino)-3,4-dioxo-cyclobut-1-enylamino]-propionic acid methyl ester Following the procedure of Method 2 above, the title compound was obtained from (2S)-3-(4-dimethylcarbamoyloxy-phenyl)-2-ethoxy-3,4-dioxo-cyclobut-1-enylamino]-propionic acid methyl ester and methyl-(3-pyridinylmethyl)amine in 82% yield as a colorless foam which was carried on immediately to the subsequent reaction.

EXAMPLE 61

(Method 3 (Modified))

(2S)-3-(4-Dimethylcarbamoyloxy-phenyl)-2-[2-(methyl-pyridin-3-ylmethyl-amino)-3,4-dioxo-cyclobut-1-enylamino]-propionic acid

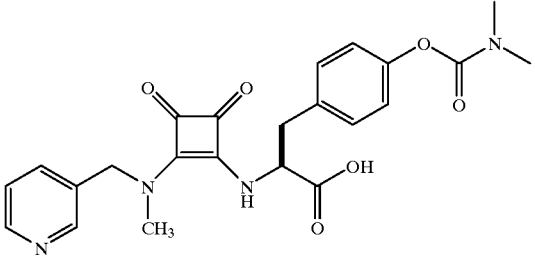

Following the procedure of Method 3 (modified) above, the title compound was obtained as its corresponding lithium salt in 88% yield as a light yellow solid.

$^1$H NMR (DMSO-d$_6$, 400 MHz) 8.50 (m, 2H), 7.67 (br m, 1H), 7.61 (d, 1H, J=7.7 Hz), 7.38 (dd, 1H, J=4.7 Hz), 7.12 (d, 2H, J=8.6 Hz), 6.88 (d, 2H, J=8.3 Hz), 4.0 (m, 2H), 4.51 (br s, 1H), 3.18 (dd, 1H, J=4.3 Hz), 3.02 (s, 3H), 2.99 (s, 3H), 2.94 (m, 1H), 2.88 (s, 3H).

MS ((+)ESI, m/e (%)) 459 (19, [M+Li]$^+$), 453 (100, [M+H]$^+$).

IR (KBr, cm$^{-1}$) 3410, 2920, 1810, 1730, 1580, 1530, 1410, 1220.

Anal. Calc'd for $C_{23}H_{23}N_4O_6Li \cdot 1.5\ H_2O$. C, 56.90; H, 5.40; N, 11.54.

Found: C, 56.63; H, 5.17; N, 11.41.

EXAMPLE 62

(Method 2)

(2S)-3-(4-Dimethylcarbamoyloxy-phenyl)-2-{2-[methyl-(2-pyridin-4-yl-ethyl)-amino]-3,4-dioxo-cyclobut-1-enylamino}-propionic acid methyl ester Following the procedure of Method 2 above, the title compound was obtained from (2S)-3-(4-dimethylcarbamoyloxy-phenyl)-2-ethoxy-3,4-dioxo-cyclobut-1-enylamino]-propionic acid methyl ester and methyl-[2-(4-pyridinyl)ethyl]amine in 77% yield as a colorless foam which was carried on immediately to the subsequent reaction.

EXAMPLE 63

(Method 3 (Modified))

(2S)-3-(4-Dimethylcarbamoyloxy-phenyl)-2-{2-[methyl-(2-pyridin-4-yl-ethyl)-amino]-3,4-dioxo-cyclobut-1-enylamino}-propionic acid

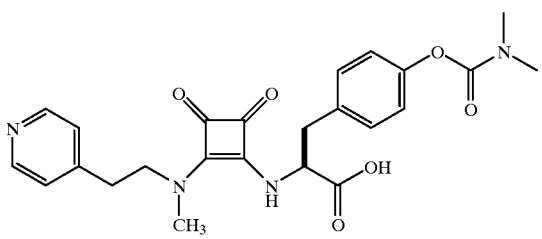

Following the procedure of Method 3 (modified) above, the title compound was obtained as its corresponding lithium salt in 88% yield as a yellow solid.

$^1$H NMR (DMSO-$d_6$, 400 MHz) δ8.41 (d, 2H, J=5.5 Hz), 7.41 (m, 1H), 7.21 (d, 2H, J=5.7 Hz), 7.09 (d, 2H, J=8.6 Hz), 6.88 (d, 2H, J=8.6 Hz), 4.37 (m, 1H), 3.70 (br m, 2H), 3.09 (m, 5H), 2.98 (s, 3H), 2.86 (s, 3H), 2.80 (br m, 2H).

MS ((+)ESI, m/e (%)) 473 (20, [M+Li]$^+$), 467 (100, [M+H]$^+$).

IR (KBr, cm$^{-1}$) 3410, 2930, 1800, 1770, 1580, 1530, 1410, 1210, 1160.

Anal. Calc'd for $C_{24}H_{25}N_4O_6Li.2.0\ H_2O$. C, 56.69; H, 5.75; N, 11.02.

Found: C, 56.82; H, 5.43; N, 10.89.

EXAMPLE 64

(Method 5)

(2S)-3-[4-(4-methylpiperazinyl)carbamoyloxy-phenyl]-2-ethoxy-3,4-dioxo-cyclobut-1-enylamino]-propionic acid methyl ester To a solution of phosgene (1.9M solution in toluene; 7.8 mmol; 4.1 mL) in $CH_2Cl_2$ (80 mL) at 0° C. was added a solution of [2-ethoxy-3,4-dioxo-cyclobut-1-enyl]-L-tyrosine methyl ester (7.8 mmol, 2.5 g) and pyridine (8.0 mmol, 633 mg; 647 μL) in $CH_2Cl_2$ (10 mL) dropwise over 15 minutes. The resulting solution was stirred at 0° C. for 30 minutes and a solution was N-methylpiperazine (11.7 mmol, 1.2 g; 1.3 mL) and pyridine (11.7 mmol, 929 mg; 950 μL) in $CH_2Cl_2$ (10 mL) was then added dropwise over 30 minutes. The resulting solution was warmed to room temperature and stirred overnight. The reaction mixture was concentrated in vacuo and the residue was partitioned between EtOAc and water. The organics were dried ($Na_2SO_4$), concentrated, and purified by falsh chromatography ($SiO_2$:5% $Et_3N$/EtOAc) to afford the title compound as a colorless foam (1.3 g; 37%).

EXAMPLE 65

(Method 2)

(2S)-3-[4-(4-methylpiperazinyl)carbamoyloxy-phenyl]-2-[2-(methyl-phenethyl-amino)-3,4-dioxo-cyclobut-1-enylamino]-propionic acid methyl ester Following the procedure of Method 2 above, the title compound was obtained from (2S)-3-[4-(4-methylpiperazinyl)carbamoyloxy-phenyl)-2-ethoxy-3,4-dioxo-cyclobut-1-enylamino]-propionic acid methyl ester and methyl-(2-phenethyl)amine in 95% yield as a colorless foam which was carried on immediately to the subsequent reaction.

EXAMPLE 66

(Method 3)

(2S)-3-[4-(4-methylpiperazinyl)carbamoyloxy-phenyl]-2-[2-(methyl-phenethyl-amino)-3,4-dioxo-cyclobut-1-enylamino]-propionic acid

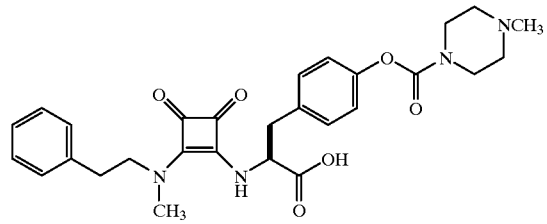

Following the procedure of Method 3 (modified) above, the title compound was obtained as its corresponding lithium salt in 90% yield as a white solid.

$^1$H NMR (DMSO-$d_6$, 400 MHz) δ7.32–7.16 (m, 6H), 7.09 (d, 2H, J=8.6 Hz), 6.90 (d, 2H, J=8.6 Hz), 4.32 (m, 1H), 3.65 (br m, 2H), 3.51 (br s, 2H), 3.38 (br s, 2H), 3.08 (m, 5H), 2.79 (br m, 2H), 2.31 (m, 4H), 2.19 (s, 3H).

MS (FAB, m/e (%)) 543 (35, (M+Na)$^+$), 527 (40, (M+Li)) 521 (100).

IR (KBr, cm$^{-1}$) 3410, 2930, 1810, 1725, 1580, 1530, 1410, 1210.

Anal. Calc'd for $C_{28}H_{31}N_4O_6Li.2.0\ H_2O$. C, 59.78; H, 6.27; N, 9.96.

Found: C, 60.04; H, 6.07; N, 9.77.

EXAMPLE 67

(Method 2)

(2S)-3-[4-(4-methylpiperazinyl)carbamoyloxy-phenyl]-2-{2-[methyl-(2-pyridin-4-yl-ethyl)-amino]-3,4-dioxo-cyclobut-1-enylamino}-propionic acid methyl ester Following the procedure of Method 2 above, the title compound was obtained from (2S)-3-[4-(4-methylpiperazinyl)carbamoyloxy-phenyl)-2-ethoxy-3,4-dioxo-cyclobut-1-enylamino]-propionic acid methyl ester and methyl-[2-(4-pyridinyl)ethyl]amine in 62% yield as a yellow foam which was carried on immediately to the subsequent reaction.

EXAMPLE 68
(Method 3 (Modified))

(2S)-3-[4-(4-methylpiperazinyl)carbamoyloxy-phenyl)-2-{2-[methyl-(2-pyridin-4-yl-ethyl)-amino]-3,4-dioxo-cyclobut-1-enylamino}-propionic acid

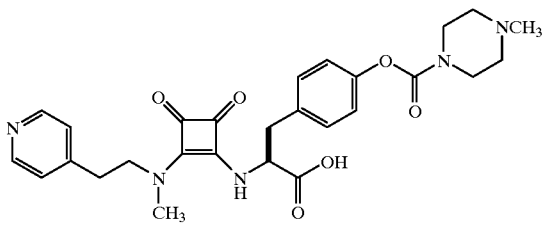

Following the procedure of Method 3 (modified) above, the title compound was obtained as its corresponding lithium salt in 80% yield as a off-white solid.

$^1$H NMR (DMSO-d$_6$, 400 MHz) δ8.41 (d, 2H, J=5.9 Hz), 7.39 (m, 1H), 7.21 (d, 2H, J=5.7 Hz), 7.09 (d, 2H, J=8.6 Hz), 6.90 (d, 2H, J=8.6 Hz), 4.38 (m, 1H), 3.69 (br m, 2H), 3.51 (br s, 2H), 3.35 (br s, 4H, under H$_2$O peak), 3.09 (m, 4H), 2.82 (m, 2H), 2.30 (m, 4H), 2.19 (s, 3H).

MS ((+)FAB, m/e (%)) 534 (100, [M+2Li]$^+$), 528 (50, [M+Li]$^+$).

IR (KBr, cm$^{-1}$) 3400 (br), 2920, 1810, 1720, 1580, 1530, 1410.

EXAMPLE 69
(Method 2)

(2S)-3-[4-(4-methylpiperazinyl)carbamoyloxy-phenyl)-2-{2-dihexylamino]-3,4-dioxo-cyclobut-1-enylamino}-propionic acid methyl ester Following the procedure of Method 2 above, the title compound was obtained from (2S)-3-[4-(4-methylpiperazinyl)carbamoyloxy-phenyl)-2-ethoxy-3,4-dioxo-cyclobut-1-enylamino]-propionic acid methyl ester and dihexylamine in 85% yield as a colorless foam which was carried on immediately to the subsequent reaction.

EXAMPLE 70
(Method 3 (Modified))

(2S)-3-[4-(4-methylpiperazinyl)carbamoyloxy-phenyl)-2-{2-dihexylamino]-3,4-dioxo-cyclobut-1-enylamino}-propionic acid Following the procedure of Method 3 (modified) above, the title compound was obtained as its corresponding lithium salt in 84% yield as a white solid.

$^1$H NMR (DMSO-d$_6$, 400 MHz) δ7.11 (d, 1H, J=6.4 Hz), 7.05 (m, 2H), 6.88 (m, 2H), 4.29 (m, 1H), 3.65 (br m, 2H), 3.55 (br s, 3H), 3.34 (br s, 4H, under H$_2$O peak), 3.12 (d, 2H, J=5.3 Hz), 2.31 (m, 4H), 2.19 (s, 3H), 1.43 (br m, 4H), 1.18 (br m, 11H), 0.82 (t, 6H, J-6.9 Hz).

MS ((+)FAB, m/e (%)) 577 (100, [M+Li]$^+$), 531 (20), 186 (45), 127 (80).

IR (KBr, cm$^{-1}$) 3410, 2920, 1810, 1580, 1520, 1410.

Anal. Calc'd for C$_{31}$H$_{45}$N$_4$O$_6$Li.1.5 H$_2$O. C, 61.68; H, 8.02; N, 9.28.

Found: C, 61.43; H, 7.78; N, 9.04.

The foregoing compounds were tested for VLA-4 binding activity using the following monvalent FACS assay. The IC$_{50}$ for a compound reflects 50% receptor occupancy. The assay can accurately measure the activity of compounds with IC$_{50}$ ranging from 0.5 nM to 1 mM.

Monovalent FACS Assay for α$_4$β$_1$ Integrin/VCAM-1 Binding

The VLA-4 binding activity of exemplary compounds was measured by measuring the inhibition of the interaction of soluble VCAM-1 with Jurkat cells (ATCC #TIB-153) which express high levels of α$_4$β$_1$ integrin (VLA-4) using a modification of the fluorescence activated cell sorter (FACS) assay described by Yednock, et al., J. Biol. Chem., 1995, 270:28740. VCAM-1 interacts with the cell surface in an α$_4$β$_1$ integrin-dependent fashion.

Jurkat cells were grown in RPMI 1640 supplemented with 10% fetal bovine serum, penicillin, streptomycin and glutamine as described by Yednock, supra.

Recombinant soluble VCAM-1 (rsVCAM-1) was produced in a baculovirus expression system as a chimeric fusion protein containing the seven immunoglobulin domains of VCAM-1 on the N-terminus and the human IgG$_1$ heavy chain constant region on the C-terminus as described by Yednock, supra. Supernatant containing approximately 10 ug/ml rsVCAM-1 was collected after 72 hours and used in the assay without purification.

Jurkat cells (approximately 10$^7$ cells/ml) were treated with 1.5 mM MnCl$_2$ and 5 μg/ml 15/7 for 30 minutes on ice to activate β$_1$ integrin. Mn$^{+2}$ activates the receptor to enhance ligand binding, and 15/7 is a monoclonal antibody that recognizes an activated/ligand occupied conformation of α$_4$β$_1$ integrin and locks the molecule into this conformation thereby stabilizing the VCAM-1/α$_4$β$_1$ integrin interaction. Yednock, et al., supra. Antibodies similar to 15/7 have

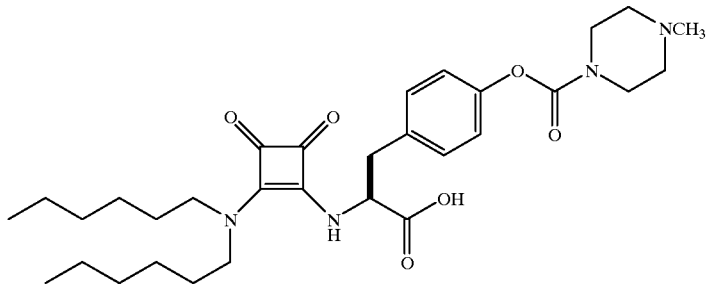

been prepared and may be used in this assay. For example, see, Luque, et al., 1996, J. Bio. Chem., 271: 11067.

Aliquots of 25 μl cells were incubated for 30 minutes at room temperature with compounds using a standard 5-point serial dilution. 15 μl of rsVCAM-Fc-containing baculovirus supernatant was added to the cells and incubated for 30 minutes on ice as described in Yednock, et al., supra.

Cells were washed twice and resuspended in 100 μl of a 1:100 dilution of FITC-conjugated goat anti-human IgG to detect the human Ig-VCAM-1 construct diluted in assay media containing 2.5% mouse serum to block potential cross-reactivity with cell surface bound 15/7. Cells were incubated on ice for 30 minutes in the dark. Cells were washed twice and analyzed with a standard FACS analysis as described in Yednock, et al., supra. on a FACScan flow cytometer (Becton Dickinson, Mountain View, Calif.). Data is shown in Table 1.

TABLE 1

| Example | IC50 (FACS) μM |
| --- | --- |
| 3 | 58 μM |
| 5 | 101 μM |
| 7 | 52 μM |
| 9 | 116 μM |
| 11 | 4.4 μM |
| 13 | 4.4 μM |
| 15 | 1.5 μM |
| 17 | 36 μM |
| 19 | 13 μM |
| 21 | 86 μM |
| 23 | 40 μM |
| 26 | 150 nM |
| 29 | 631 nM |
| 32 | 12 nM |
| 35 | 15 nM |
| 37 | 2.2 nM |
| 39 | 1.3 nM |
| 41 | 26 nM |
| 44 | 6.5 nM |
| 46 | 40 nM |
| 48 | 160 nM |
| 50 | 9 μM |
| 53 | 71 nM |
| 57 | 0.9 nM |
| 59 | 0.6 nM |
| 61 | 8.3 nM |
| 63 | 1.6 nM |
| 66 | 0.5 nM |
| 68 | 1.3 nM |
| 70 | 0.2 nM |

Thus, compounds of the present invention exhibit high affinity for VLA-4, and can effectively inhibit the interaction of VLA-4 with VCAM. The compounds are useful for the treatment of inflammatory and autoimmune diseases including, but not limited to multiple sclerosis, meningitis, asthma, Alzheimer's disease, atherosclerosis, AIDS dementia, diabetes, inflammatory bowel syndrome, rheumatoid arthritis, tumor metastasis, tissue transplantation, and myocardial ischemia.

The compounds of the present invention can be used in the form of salts derived from pharmaceutically or physiologically acceptable acids or bases. These salts include, but are not limited to, salts with inorganic acids such as hydrochloric acid, sulfuric acid, nitric acid, phosphoric acid and salts with organic acids such as acetic acid, oxalic acid, succinic acid, and maleic acid. Other salts include salts with alkali metals or alkaline earth metals, such as sodium, potassium, calcium or magnesium. The compounds of the present invention can also be used in the form of esters at the C-terminus; carbamates, amides and the like at the N-terminus or other conventional "pro-drug" forms which, when administered, convert to the active moiety in vivo.

Compounds of the present invention may be administered in combination with one or more pharmaceutically acceptable carriers, for example, solvents, diluents and the like. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils. Adjuvents customarily employed in the preparation of pharmaceutical compositions may be advantageously included, such as flavoring agents, coloring agents, preserving agents, and antioxidants, for example, vitamin E, ascorbic acid, BHT and BHA. These compounds may be administered orally as well as by intravenous, intramuscular, or subcutaneous routes. When administered orally in such forms as tablets, capsules, dispersible powders, granules, or suspensions, formulations may contain, for example, from about 0.05 to 5% of suspending agent, syrups containing, for example, from about 10 to 50% of sugar, or elixirs containing, for example, from about 20 to 50% ethanol, and the like. When administration is parenterally, formulation may be, for example, sterile injectable solutions or suspensions containing from about 0.05 to 5% suspending agent in an isotonic medium. Such pharmaceutical preparations may contain, for example, from about 25 to about 90% by weight of active ingredient in combination with a carrier, and more preferably between about 5% and 60% by weight of active ingredient.

The preferred pharmaceutical compositions from the standpoint of ease of preparation and administration are solid compositions, particularly tablets and hard-filled or liquid-filled capsules. Oral administration of the compounds is preferred.

The dosage requirements can be determined by one skilled in the art and will vary with the particular composition employed, the route of administration, the severity of the symptoms presented and the particular subject being treated.

What is claimed is:

1. A compound of the formula:

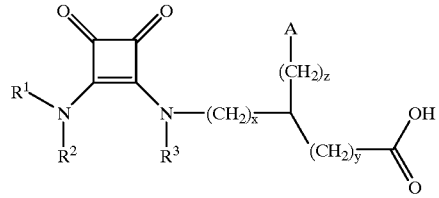

wherein
R$^1$ is alkyl, aryl, heteroaryl, aralkyl or heteroaralkyl;
R$^2$ is H, alkyl, aryl, heteroaryl, aralkyl, or heteroaralkyl; or
R$^1$ and R$^2$ may be taken together to form a saturated or unsaturated heterocyclic ring;
R$^3$ is H, alkyl, aryl, heteroaryl, aralkyl, or heteroaralkyl;
A is aryl or heteroaryl; and
x, y and z are independently 0, 1, 2, 3,
or a pharmaceutical salt thereof.

2. The compound of claim 1 wherein A is phenyl, R1 is alkyl, R2 and R3 are H, x and y are 0 and z is 1.

3. The compound of claim 2 wherein A is substituted phenyl.

4. The compound of claim 1 wherein A is phenyl, R1 is heteroaralkyl, R2 and R3 are H, x and y are 0 and z is 1.

5. The compound of claim 1 wherein A is substituted aryl and the substituent is OCONR6R7.

6. A compound of claim 1 which is [2-(benzylamino)-3,4-dioxo-cyclobut-1-enyl]-L-phenylalanine; or a pharmaceutical salt thereof.

7. A compound of claim 1 which is [2-(benzhydrylamino)-3,4-dioxo-cyclobut-1-enyl]-L-phenylalanine; or a pharmaceutical salt thereof.

8. A compound of claim 1 which is 2-{2-[2-(1H-Indol-3-yl)-ethylamino]-3,4-dioxo-cyclobut-1-enylamino}-L-phenylalanine; or a pharmaceutical salt thereof.

9. A compound of claim 1 which is {3,4-dioxo-2-](pyridin-3-ylmethyl)-amino]-cyclobut-1-enyl}-L-phenylalanine; or a pharmaceutical salt thereof.

10. A compound of claim 1 which is [2-(benzyl-hexyl-amino)-3,4-dioxo-cyclobut-1-enyl]-L-phenylalanine; or a pharmaceutical salt thereof.

11. A compound of claim 1 which is (2-dibenzylamino-3,4-dioxo-cyclobut-1-enylamino)-L-phenylalanine; or a pharmaceutical salt thereof.

12. A compound of claim 1 which is (S)-2-(2-dihexylamino-3,4-dioxo-cyclobut-1-enylamino)-3-phenyl-propionic acid; or a pharmaceutical salt thereof.

13. A compound of claim 1 which is (S)-2-[2-(hexyl-naphthalen-2-ylmethyl-amino)-3,4-dioxo-cyclobut-1-enylamino]-3-phenyl-propionic acid; or a pharmaceutical salt thereof.

14. A compound of claim 1 which is (S)-2-{2-[(4-dimethylamino-benzyl)-hexyl-amino]-3,4-dioxo-cyclobut-1-enylamino}-3-phenyl-propionic acid; or a pharmaceutical salt thereof.

15. A compound of claim 1 which is N-[3,4-dioxo-2-(4-phenyl-piperazin-1-yl)-cyclobut-1-en-1-yl]-L-phenylalanine; or a pharmaceutical salt thereof.

16. A compound of claim 1 which is (S)-2-[2-(4-acetyl-piperazin-1-yl)-3,4-dioxo-cyclobut-1-enylamino]-3-phenyl-propionic acid; or a pharmaceutical salt thereof.

17. A compound of claim 1 which is (S)-3-(4-benzoylamino-phenyl)-2-(2-dihexylamino-3,4-dioxo-cyclobut-1-enylamino)-propionic acid; or a pharmaceutical salt thereof.

18. A compound of claim 1 which is (S)-3-(1-benzyl-1H-imidazol-4-yl)-2-(2-dihexylamino-3,4-dioxo-cyclobut-1-enylamino)-propionic acid; or a pharmaceutical salt thereof.

19. A compound of claim 1 which is N-(2-dihexylamino-3,4-dioxo-cyclobut-1-enylamino)-O-(3-dimethylamino-propyl)-L-tyrosine; or a pharmaceutical salt thereof.

20. A compound of claim 1 which is N-[2-[methyl[2-(4-pyridinyl)ethyl]amino]-3,4-dioxo-1-cyclobuten-1-yl]-4-[(4-pyridinylcarbonyl)amino]-L-phenylalanine; or a pharmaceutical salt thereof.

21. A compound of claim 1 which is N-[2-[methyl(2-phenylethyl)amino]-3,4-dioxo-1-cyclobuten-1-yl]-4-[(4-pyridinylcarbonyl)amino]-L-phenylalanine; or a pharmaceutical salt thereof.

22. A compound of claim 1 which is N-[2-(dihexylamino)-3,4-dioxo-1-cyclobuten-1-yl]-4-[(4-pyridinylcarbonyl)amino]-L-phenylalanine; or a pharmaceutical salt thereof.

23. A compound of claim 1 which is N-[2-(methyl-pyridin-3-ylmethyl-amino)-3,4-dioxo-cyclobut-1-enyl]-4-[(pyridine-4-carbonyl)-amino]-L-phenylalanine; or a pharmaceutical salt thereof.

24. A compound of claim 1 which is N-[2-(dihexylamino)-3,4-dioxo-1-cyclobuten-1-yl]-4-[(3-pyridinylcarbonyl)amino]-L-phenylalanine; or a pharmaceutical salt thereof.

25. A compound of claim 1 which is N-[2-[methyl[2-(4-pyridinyl)ethyl]amino]-3,4-dioxo-1-cyclobuten-1-yl]-4-[(3-pyridinylcarbonyl)amino]-L-phenylalanine; or a pharmaceutical salt thereof.

26. A compound of claim 1 which is N-[2-(methyl-pyridin-3-ylmethyl-amino)-3,4-dioxo-cyclobut-1-enyl]-4-[(pyridine-3-carbonyl)-amino]-L-phenylalanine; or a pharmaceutical salt thereof.

27. A compound of claim 1 which is N-{2-[methyl-(2-pyridin-4-yl-ethyl)-amino]-3,4-dioxo-cyclobut-1-enyl}-L-phenylalanine; or a pharmaceutical salt thereof.

28. A compound of claim 1 which is N-[2-(dihexylamino)-3,4-dioxo-1-cyclobuten-1-yl]-{4-[4-(N-carboxybenzoyl)-piperidinylcarbonyl]amino}-L-phenylalanine methyl ester; or a pharmaceutical salt thereof.

29. A compound of claim 1 which is (2S)-3-(4-dimethylcarbamoyloxy-phenyl)-2-[2-(methyl-phenethyl-amino)-3,4-dioxo-cyclobut-1-enylamino]-propionic acid; or a pharmaceutical salt thereof.

30. A compound of claim 1 which is (2S)-2-(2-dihexylamino-3,4-dioxo-cyclobut-1-enylamino)-3-(4-dimethylcarbamoyloxy-phenyl)-propionic acid; or a pharmaceutical salt thereof.

31. A compound of claim 1 which is (2S)-3-(4-dimethylcarbamoyloxy-phenyl)-2-[2-(methyl-pyridin-3-ylmethyl-amino)-3,4-dioxo-cyclobut-1-enylamino]-propionic acid; or a pharmaceutical salt thereof.

32. A compound of claim 1 which is (2S)-3-(4-dimethylcarbamoyloxy-phenyl)-2-{2-[methyl-(2-pyridin-4-yl-ethyl)-amino]-3,4-dioxo-cyclobut-1-enylamino}-propionic acid; or a pharmaceutical salt thereof.

33. A compound of claim 1 which is (2S)-3-[4-(4-methylpiperazinyl)carbamoyloxy-phenyl]-2-[2-(methyl-phenethyl-amino)-3,4-dioxo-cyclobut-1-enylamino]-propionic acid; or a pharmaceutical salt thereof.

34. A compound of claim 1 which is (2S)-3-[4-(4-methylpiperazinyl)carbamoyloxy-phenyl]-2-{2-[methyl-(2-pyridin-4-yl-ethyl)-amino]-3,4-dioxo-cyclobut-1-enylamino}-propionic acid; or a pharmaceutical salt thereof.

35. A compound of claim 1 which is (2S)-3-[4-(4-methylpiperazinyl)carbamoyloxy-phenyl]-2-{2-dihexylamino]-3,4-dioxo-cyclobut-1-enylamino}-propionic acid; or a pharmaceutical salt thereof.

36. A method for inhibiting leukocyte adhesion in a patient suffering from a condition associated with leukocyte adhesion comprising administering to the patient a therapeutically effective amount of a compound of the formula:

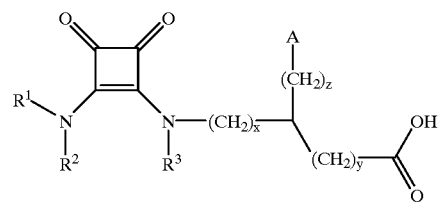

wherein
R¹ is alkyl, aryl, heteroaryl, aralkyl or heteroaralkyl;
R² is H, alkyl, aryl, heteroaryl, aralkyl, or heteroaralkyl; or
R¹ and R² may be taken together to form a saturated or unsaturated heterocyclic ring;
R³ is H, alkyl, aryl, heteroaryl, aralkyl, or heteroaralkyl;
A is aryl or heteroaryl; and
x, y and z are independently 0, 1, 2, 3, or a pharmaceutical salt thereof.

37. A method of treating a patient suffering from an inflammatory diseases comprising administering to the patient a therapeutically effective amount of a compound of the formula:

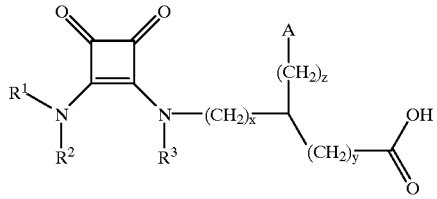

wherein
$R^1$ is alkyl, aryl, heteroaryl, aralkyl or heteroaralkyl;
$R^2$ is H, alkyl, aryl, heteroaryl, aralkyl, or heteroaralkyl; or
$R^1$ and $R^2$ may be taken together to form a saturated or unsaturated heterocyclic ring;
$R^3$ is H, alkyl, aryl, heteroaryl, aralkyl, or heteroaralkyl;
A is aryl or heteroaryl; and
x, y and z are independently 0, 1, 2, 3,
or a pharmaceutical salt thereof.

38. The method of claim 36 wherein the inflammatory disease is selected from the group consisting multiple sclerosis, meningitis, asthma, Alzheimer's disease, atherosclerosis, AIDS dementia, diabetes, inflammatory bowel syndrome, rheumatoid arthritis, tumor metastasis, tissue transplantation, and myocardial ischemia.

39. A pharmaceutical composition comprising a compound of the formula:

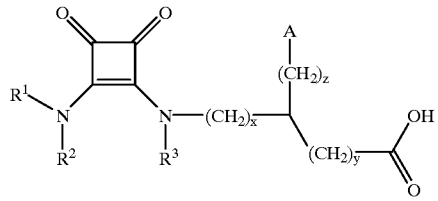

wherein
$R^1$ is alkyl, aryl, heteroaryl, aralkyl or heteroaralkyl;
$R^2$ is H, alkyl, aryl, heteroaryl, aralkyl, or heteroaralkyl; or
$R^1$ and $R^2$ may be taken together to form a saturated or unsaturated heterocyclic ring;
$R^3$ is H, alkyl, aryl, heteroaryl, aralkyl, or heteroaralkyl;
A is aryl or heteroaryl; and
x, y and z are independently 0, 1, 2, 3,
and a pharmaceutically acceptable carrier.

* * * * *